(12) United States Patent
Newberg

(10) Patent No.: US 7,389,792 B2
(45) Date of Patent: *Jun. 24, 2008

(54) DIP TUBE VALVE ASSEMBLY

(75) Inventor: Douglas A. Newberg, Plainsboro, NJ (US)

(73) Assignee: NL Technologies, Ltd., Princeton, NJ (US)

( * ) Notice: Subject to any disclaimer, the term of this patent is extended or adjusted under 35 U.S.C. 154(b) by 593 days.

This patent is subject to a terminal disclaimer.

(21) Appl. No.: 10/388,409

(22) Filed: Mar. 17, 2003

(65) Prior Publication Data

US 2004/0016460 A1 Jan. 29, 2004

Related U.S. Application Data

(63) Continuation-in-part of application No. 10/056,482, filed on Jan. 28, 2002, now Pat. No. 6,532,981, which is a continuation of application No. 09/471,252, filed on Dec. 23, 1999, now Pat. No. 6,345,640.

(60) Provisional application No. 60/113,936, filed on Dec. 24, 1998.

(51) Int. Cl.
F16K 1/44 (2006.01)
F16K 37/00 (2006.01)

(52) U.S. Cl. ............... 137/551; 137/563; 137/240; 251/144; 73/863.86

(58) Field of Classification Search .......... 137/240, 137/563, 597, 15.05, 551; 239/125; 251/144, 251/335.2; 73/863.86
See application file for complete search history.

(56) References Cited

U.S. PATENT DOCUMENTS

| | | | |
|---|---|---|---|
| 711,609 A | 10/1902 | Woodnall | |
| 1,351,780 A | 9/1920 | Mead | |
| 1,397,220 A | 11/1921 | Lord | |
| 2,401,124 A * | 5/1946 | Walker et al. | 141/37 |
| 2,841,314 A | 7/1958 | Munson et al. | |
| 3,523,549 A | 8/1970 | Anderson | |
| 3,693,647 A | 9/1972 | Saar | |
| 3,871,400 A | 3/1975 | Thastrup | |
| 4,346,611 A | 8/1982 | Welker | |
| 4,365,747 A * | 12/1982 | Knapp et al. | 239/125 |
| 4,458,543 A | 7/1984 | Mieth | |
| 4,497,341 A * | 2/1985 | Wright | 137/563 |
| 4,643,218 A | 2/1987 | Reed, Jr. | |

(Continued)

FOREIGN PATENT DOCUMENTS

DE 30 43 836 A 9/1981

*Primary Examiner*—John Rivell
*Assistant Examiner*—Cloud K Lee
(74) *Attorney, Agent, or Firm*—Birch, Stewart, Kolasch & Birch, LLP

(57) ABSTRACT

An apparatus for sampling or feeding a flowable material through a wall of a vessel or conduit includes a body having a collection chamber formed therein. A passage has an opening operatively connected to the collection chamber. An orifice is formed in the body and is in communication with the collection chamber. The orifice is located generally adjacent the opening of the passage. A sealing device is mounted to the body to seal and unseal said orifice. Furthermore, at least a portion of the opening of the passage is located flush with or on a process side of the wall of the vessel or conduit when the apparatus is mounted to the wall of the vessel or conduit.

8 Claims, 16 Drawing Sheets

U.S. PATENT DOCUMENTS

| | | | |
|---|---|---|---|
| 4,702,114 A | 10/1987 | Cabannes | |
| 4,702,275 A | 10/1987 | Ballun et al. | |
| 4,708,160 A | 11/1987 | Sharp et al. | |
| 4,726,933 A * | 2/1988 | Mayr et al. | 422/133 |
| 4,804,164 A | 2/1989 | Nakazawa et al. | |
| 4,822,570 A | 4/1989 | Lerman et al. | |
| 4,909,271 A | 3/1990 | Canaan et al. | |
| 4,911,412 A | 3/1990 | Danko | |
| 5,096,029 A | 3/1992 | Bauer et al. | |
| 5,152,500 A * | 10/1992 | Hoobyar et al. | 251/269 |
| 5,296,197 A | 3/1994 | Newberg et al. | |
| 5,370,146 A | 12/1994 | King et al. | |
| 5,372,782 A | 12/1994 | Karkantis et al. | |
| 5,465,768 A | 11/1995 | DeRoos et al. | |
| 5,525,301 A | 6/1996 | Newberg et al. | |
| 5,695,120 A * | 12/1997 | Kingsford | 239/112 |
| 5,786,209 A | 7/1998 | Newberg | |
| 5,794,644 A | 8/1998 | Paylor | |
| 5,823,222 A | 10/1998 | Minshull et al. | |
| 6,133,022 A | 10/2000 | Newberg | |
| 6,182,685 B1 | 2/2001 | Goff et al. | |
| 6,279,603 B1 * | 8/2001 | Czarnik et al. | 137/339 |
| 6,345,640 B1 * | 2/2002 | Newberg | 137/15.05 |
| 6,491,283 B2 | 12/2002 | Newberg | |
| 6,532,981 B2 * | 3/2003 | Newberg | 137/15.05 |
| 2002/0185626 A1 | 12/2002 | Newberg | |

* cited by examiner

DIP TUBE VALVE ASSEMBLY

CROSS-REFERENCE TO RELATED APPLICATIONS

This application is a Continuation-In-Part of U.S. application Ser. No. 10/056,482 filed on Jan. 28, 2002, now U.S. Pat. No. 6,532,981, which is a Continuation of U.S. application Ser. No. 09/471,252 filed on Dec. 23, 1999, now U.S. Pat. No. 6,345,640. This application also claims priority under 35 U.S.C. § 119 on U.S. Provisional Application No. 60/113,936 filed on Dec. 24, 1998. The entirety of each of the above documents is hereby incorporated by reference.

BACKGROUND OF THE INVENTION

1. Field of the Invention

The present invention relates to the field of sampling, feeding or inoculating of material from or to a vessel or conduit.

2. Description of Related Art

Quality products require precise control of many phases of a production process. It is also true that it is necessary to maintain the integrity of the process and to protect the surroundings from the process. While many advances have been made in the development of sensors for measuring the condition of a specific process on-line which will aid in maintaining this process integrity, many of the characteristics of processes still need to be measured off-line through the physical and/or chemical analysis of an actual sample of the process. The removal of the sample from the process has to be conducted in a way that will preserve the integrity of the process, the surrounding environment as well as the integrity and character of the sample itself.

In a related but different procedure, many processes require inoculation of seed organisms or catalysts into a process to initiate the conversion of a set of substrate materials into other process intermediates or a final product or set of products. Sometimes this seed material is a live organism, a component of a live organism or another form of catalyst. In any case, these materials frequently need to be added to a process in a way that maintains the integrity of the process, the materials being added and their source, the integrity of the surrounding environment, or, perhaps, all of these.

There are examples of devices in the prior art that provide a means to deliver or withdraw materials from a process while maintaining the integrity of the process, the sample or the feed material or the surrounding environment but these devices are restricted in their effectiveness, particularly in their abilities to maintain the integrity or character of either the sampled material or material being added to the process because these devices have designs that are optimized for use in certain physical orientations. When used in orientations other than those they are designed for, these devices frequently suffer from the presence of crevices, particularly between component joints exposed to the process, and from design features that inhibit free flow and drainage of flowable materials through the device, resulting in pooling within the device. Both the crevices and pooling phenomena result in material carryover from one sampling, feeding or inoculation episode to the next, causing the deterioration in quality of any subsequent material introduced through sampling, feeding or inoculating into these devices.

It is also the case that some of these devices are not designed to be reused or, if they are designed for reuse, must be removed from the process and cleaned and sometimes resterilized before being able to be used again with the process.

There is a need for an apparatus that can be fitted, either permanently or removably, into a process which will allow materials to be fed, inoculated to or sampled from a process through a device principally designed to provide access to the process from above but which may provide reasonably good access to a process when installed at angles from vertical to horizontal. It is also desirable that an embodiment of this device provide a means by which it can be washed and sterilized in place and a means by which the thermal and electrical conditions inside the device be generally insulated from those of the process into which it is inserted. It is further desirable that the device, when placed in installations from vertical to horizontal relative to the process, be able to accumulate flowable materials occurring in the device in an area where they may be expelled or washed out by the introduction of other flowable materials under pressure coming either from the process or a second source through another access into the device.

In the existing art, there are examples of devices that provide a means for adding materials to the process but do not provide a means for washing and resterilizing in place and for effectively draining sampled material or cleansing, rinsing or sterilizing solutions from within the device.

Referring to FIG. 15 of the present invention, a description of a Background Art device will be described. The Background Art device consists, in essence, of a pipe section 300 mounted through the wall of a vessel or conduit 301. One end 303 of the pipe section 300 opens into the process contained in the vessel or conduit 301 and the other end 305 opens to a supply located outside the vessel or conduit 301. Flow into or out of the vessel or conduit 301 is controlled by a flow control valve 307 mounted outside the vessel or conduit 301 at a position intermediate between the supply and the outer wall of the vessel or conduit 301.

The above design approach is universally used for making additions and, in many cases, withdrawals from processes because it is simple, easily maintained, cost effective to purchase and operate and lends itself easily to a wide range of desirable processing upgrades, redundancies and controls. For sanitary or aseptic processing, the most important of these may be the ease with which seal redundancy (in the form of redundant in-line flow control valves) and secondary valving (for in-place cleaning and sterilizing) can be designed and added to the basic in-line flow control valve 307.

For example, referring to FIG. 15 again, a secondary flow control valve 309 can easily be added to obtain a redundant seal. The portion 314 of the pipe section 300 upstream of the secondary flow control valve 309 can easily be cleaned by a supply of material through the opening 305 and out of the drain passage 315 when the secondary flow control valve 309 is closed and the valve 317 is open. In addition, the portion 316 of the pipe section 300 between the secondary flow control valve 309 and the seal of the primary flow control valve 307 can be easily cleaned by closing the secondary flow control valve 309 and opening the valve 319 in the inlet passage 321 and the valve 325 in the drain passage 323. Therefore, flow through the inlet passage 321, the portion 316 and out of the drain passage 323.

Today, the average cost of valves is decreasing, while the average cost of failed batches of process is increasing. Therefore, it is not surprising to one familiar with industrial production today to see the great proliferation and sophistication of primary and secondary redundant valving systems being designed and installed in an effort to ensure better monitoring, control and maintenance of the environment around the primary flow control seal with the process and a secondary redundant seal, when present, as well as the environment between the two valve seals in an effort to protect and ensure the quality and integrity of the process.

In spite of all of the design effort and expense going into development and installation of evermore elaborate conventional external in-line valving systems to control flow into vessels (and contain the process within), no comprehensive solution has yet been offered to rid production systems of the deadspace 311 that occurs between the seal of the primary flow control valve 307 and the opening 303 of the pipe section 300. Without the availability of such a device, there is also no device available that allows, nor has a device or system been made available that would permit periodic recleaning and resterilizing of such a deadspace 311 within the production environment periodically during production runs. As a consequence, any type of supply port 313 into a vessel or conduit 301, including gas sparging devices, may experience stagnation, material build-up and line blockages, particularly during extended production runs. Since blockages become more severe with time, the inability to intermitently reclean and/or resterilized to remove blockages and restore full flow capacity can significantly diminish the operator's ability to control and optimize the process.

Eliminating the risk to the process posed by an uncleanable deadspace 311 currently existing in supply port systems as well as many sample capture or harvesting valve systems would be an important step in assuring the quality and productivity of processes. Ideally the solution should be done without losing the advantages offered by current supply port system designs, including the ability to clean and steam sterilize the upstream portion 316 of the seal of the primary flow control valve 307 with the process while it remains on-going, the ability to design in flow control valve redundancy and the ability to monitor, control and maintain the environment between primary and secondary (redundant) flow control valve seals. It is also of value for the solutioin to be usable in a variety of process applications that are heat sensitive without damaging those processes.

SUMMARY OF THE INVENTION

Accordingly, it is an object of the present invention to provide a device which allows for the feeding or inoculating of a material into a process, and which can be easily washed and resterilized in place.

It is another object of the present invention to provide a device which can best be used in an orientation from the vertical to the horizontal and which can still effectively drain sampled material or cleansing, rinsing or sterilizing solutions from within the device.

It is a further object of the present invention to provide a device which enhances the free flow of material through the device in order to prevent the pooling of the material within the device. This prevents the contamination of the sampled material, material added to the process, or the process itself.

It is yet another object of the present invention to provide a device which can be reused over and over again, and which can be cleaned or sterilized without having to remove the device from the process.

The valve of the present invention is designed primarily to take samples from a vertical installation although it can be used effectively at angles of installation down to horizontal. The valve works by providing a collection basin or well at a lower portion of the collection chamber of the valve body of the dip tube valve assembly. A drain passage opening is provided adjacent to the opening of the orifice where the orifice opens into the collection chamber in the valve body. By arranging the opening to the drain passage even with or lower than the inside margin of the orifice opening, a flowable material inside the valve body, including the collection chamber, the inlet or drain passages, will drain down into the opening of the drain passage. When this valve is installed at a positive angle from the horizontal, up to and including the vertical, sample material will not passively drain out of it but it can be forced up and out the designated drain passage. When forced evacuation is to be used, the position of the opening to the drain passage becomes less critical so long as it is positioned so that it may receive unobstructed flow from within the chamber.

Material may be sampled through the valve by supplying overpressure to force material inside the vessel or conduit through the orifice and up and out through the drain passage. However, once the orifice is closed, this material will flow back down into the collection chamber of the valve. In order to fully remove sampled material from within the valve a flowable material must be fed through the inlet passage into the collection chamber after the sampling orifice has been resealed. The introduction of this material will displace or flush the sampled material collected in the bottom of the collection chamber, forcing the sampled material up and out of valve through the drain passage.

The collection basin or well formed at the bottom of the collection chamber enhances the removal of the sampled material, since the material remaining in the collection chamber flows into the collection basin or well to adjacent the opening of the drain passage. Therefore, when the flowable material is provided through the inlet, the sampled material which has collected at the opening of the drain passage can be easily removed.

In an embodiment of the present invention, the axis of the inlet can be oriented non-parallel to a plane passing through the major diameter of an embodiment with a round internal collection chamber. This off-center introduction of the flowable material will help create a vortex flow through the collection chamber, scouring the surfaces of the chamber and forcing any flowable material therein down to the opening in the drain passage and then up and out through the drain passage. The creation of a vortex may be further enhanced by offsetting the opening laterally.

In another embodiment of the present invention, the opening of the drain passage can be oriented in a similar but opposing fashion so as to open into the vortexing flow. The effect of this is to sweep material down, into and then up and out of the drain passage. This passage opening may also be offset laterally.

While the valve of the present invention is similar in many aspects to sample valve embodiments previously disclosed, one of which is the dependence on gravity to direct the flow of material down through the collection chamber and then down into the drain passage opening, the valve of the present invention differs in that previous designs were only capable of supplying the sampled material out of the valve through the drain passage to a sample vial simply by means of gravity flow. The dip tube valve assembly of the present invention; however, includes an active scouring motion provided by a second flowable material supplied through the inlet passage to generally remove and deliver all of the sampled material up through and out of the drain passage to a sample vial.

It should be noted that the device of the present invention can be used for sampling a material without an inlet passage. This can be accomplished through the use of over-pressure of the source of sampled material alone or through the use of over-pressured sample material followed by a second flowable material through the sampling orifice. While in the second instance, all of the sampled material might be removed up through the drain passage to a sample vial, in the first instance, once the sampling orifice is resealed, sampled materials in the interstices of the valve remain in the valve until either the next sampling episode or until other active methods are used to remove them.

The above objects have been accomplished by the dip tube valve assembly of the present invention. An apparatus for sampling or feeding a flowable material through a wall of a vessel or conduit includes a body; a collection chamber formed in said body; a drain passage, said drain passage having an opening operatively connected to said collection chamber; an orifice formed in said body and in communication with said collection chamber, said orifice being located generally adjacent the opening of the drain passage; and a sealing device for sealing and unsealing said orifice.

In addition to the above, the present inventor would like to propose a device with features that address the problems associated with the Background Art supply port design. To begin with, the problems associated with the current supply port design can be partially rectified by moving the seal of the primary flow control valve from outside the vessel or conduit to a position on the pipe section where it opens to the process at. Installing such a tip-sealing device will eliminate the deadspace from the process side of the system but it does not remove the deadspace from the system. In fact, the deadspace remains within the same portion of the pipe section but the blind end has been switched to the other (non-process) side. While eliminating the deadspace from the process side may be preferable to having it continuously facing into the process, plaque build-up, sample quality deviation and other problems associated with the deadspace still remain since, when the tip seal is reopened this deadspace will be reintroduced to the process. The larger the internal deadspace volume, the larger the threat to the process.

In view of the above, there is a need for a device where the seal is moved from a position outside the vessel or conduit to a position adjacent the process. There is also a need to provide a means to clean-in-situ and, in some cases, to sterilize-in-situ behind this seal, on the non-process side. There is a further need for a device with these capabilities in addition to protecting a heat-sensitive process from exposure to excessive heat during recleaning and resterilizing performed while the production is on-going. There is also the need to provide seal redundancy as well as a means to detect seal failure, either actively or passively. It is also desirable, in some circumstances, to be able to adjust valve seating while in others for this function to be performed passively. Finally, because certain types of seals provide superior service in different processes, it is desirable that the suggested design approach lend itself to different sealing systems.

The above aspects of the present invention are accomplished by providing an apparatus for sampling or feeding a flowable material through a wall of a vessel or conduit comprising:

a body;

a collection chamber formed in said body;

a passage, said passage having an opening operatively connected to said collection chamber;

an orifice formed in said body and in communication with said collection chamber, said orifice being located generally adjacent the opening of the passage; and a sealing device, said sealing device being mounted to said body to seal and unseal said orifice, wherein at least a portion of said opening of said passage is located flush with or on a process side of the wall of the vessel or conduit when the apparatus is mounted to the wall of the vessel or conduit.

The above aspects of the present invention can also be accomplished by providing an apparatus for sampling or feeding a flowable material through a wall of a vessel or conduit comprising:

a body;

a collection chamber formed in said body;

a passage, said passage having an opening operatively connected to said collection chamber;

an orifice formed in said body and in communication with said collection chamber, said orifice being located generally adjacent the opening of the passage; and a sealing device, said sealing device being mounted to said body to seal and unseal said orifice; and a porous element, said porous element being located in said opening of said passage, wherein the flowable material is a gas.

The above aspects of the present invention can also be accomplished by providing an apparatus for sampling or feeding a flowable material through a wall of a vessel or conduit comprising:

a body;

a primary collection chamber formed in said body;

a primary passage, said primary passage having an opening operatively connected to said primary collection chamber;

a secondary collection chamber formed in said body; and a secondary passage, said secondary passage having an opening operatively connected to said secondary collection chamber;

an orifice formed in said body and in communication with said collection chamber, said orifice being located generally adjacent the opening of the passage; and a sealing device, said sealing device being mounted to said body to seal and unseal said orifice.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENTS

Figure 1:
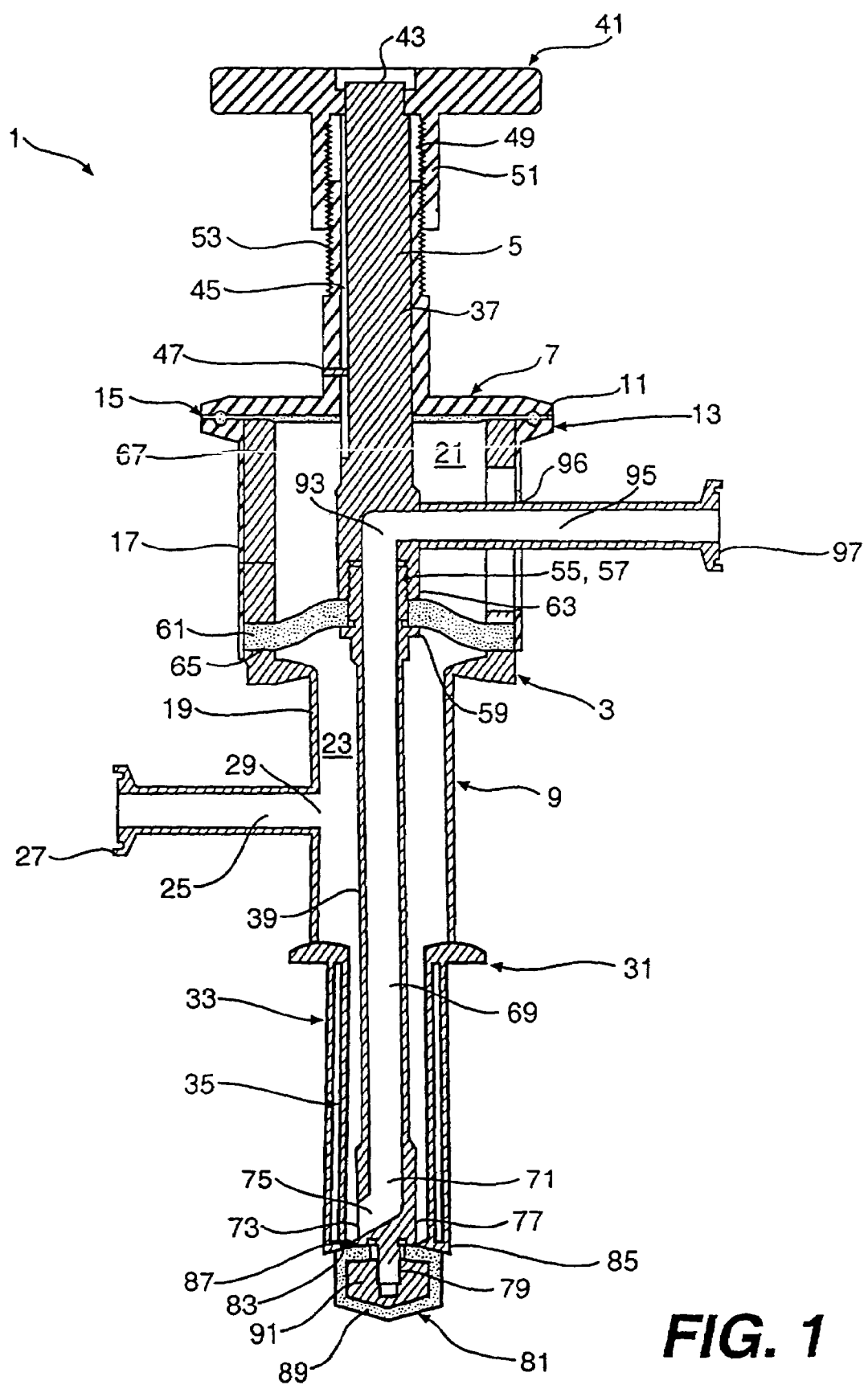
FIG. 1 is a cross-section of the first embodiment of the dip tube valve assembly of the present invention, wherein the valve is in the closed position.

The present invention will now be described with reference to the accompanying drawing. The same reference numerals have been used throughout the several views in order to identify the same or similar elements.

Figure 2:
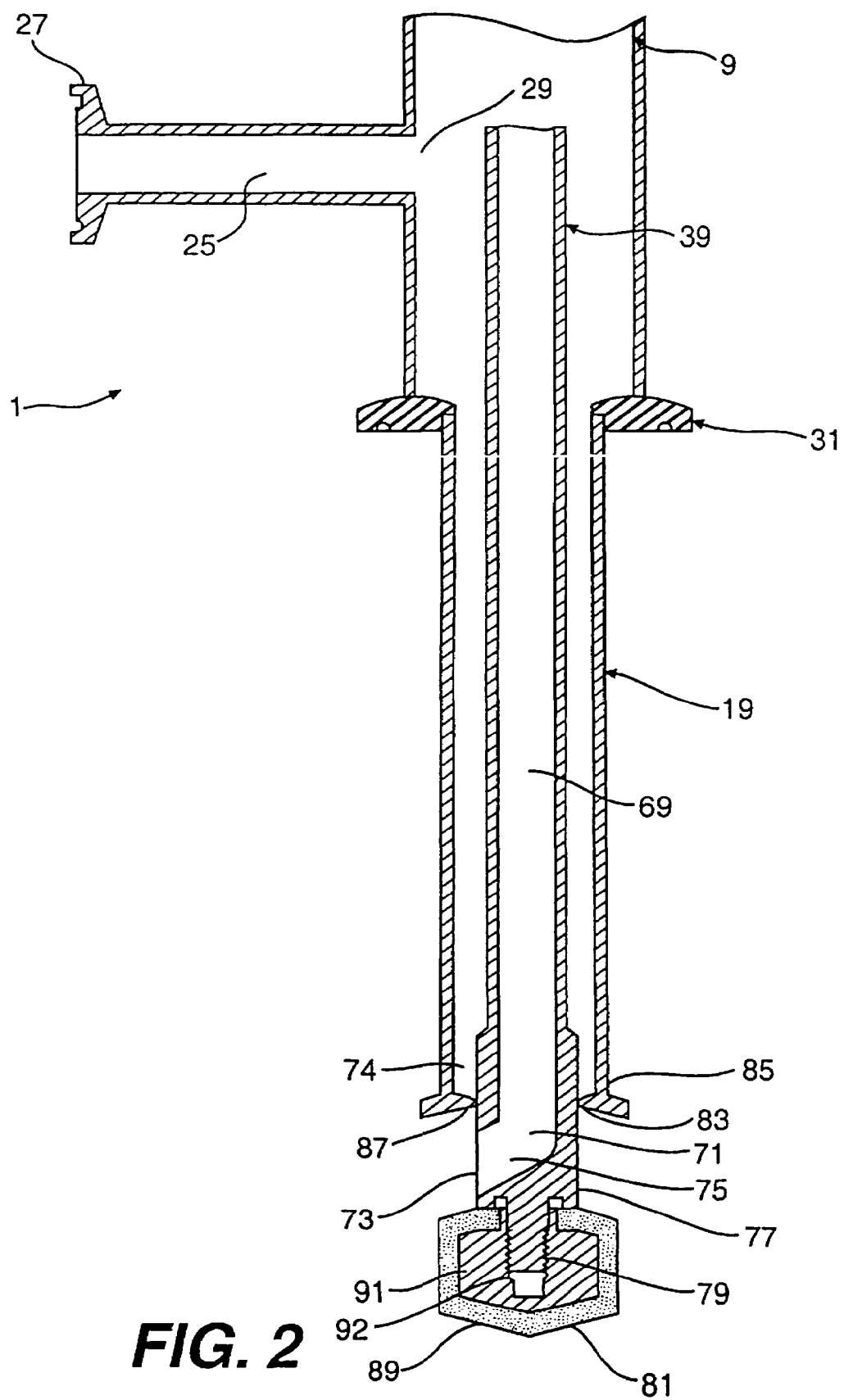
FIG. 2 is a detail of a lower portion of the embodiment of FIG. 1, wherein the valve is in the open position and no insulating jacket is included.

A first embodiment of the present invention will now be described with reference to FIGS. 1 and 2. FIG. 1 illustrates a cross-section of the first embodiment of the dip tube valve assembly of the present invention, wherein the valve is in the closed position. FIG. 2 is a detail of a lower portion of the embodiment of FIG. 1, wherein the valve is in the open position and no insulating jacket is included.

Referring to FIG. 1, the dip tube valve assembly 1 includes a body 3 and a valve operating rod or shaft 5 mounted for reciprocation within the body 3.

In the first embodiment, the body 3 includes a housing top 7 and a housing base 9 connected to each other through mutually engageable flanges 11 and 13 formed on the housing top 7 and housing base 9, respectively. The flanges are preferably secured together by a clamp (not illustrated); however, any other fastening means can be used, such as a plurality of bolts extending through holes formed in the perimeter of the flanges 11 and 13. A gasket 15 may be located between the flanges 11 and 13 in order to provide a sealed connection between the housing top 7 and the housing base 9.

The housing base 9 includes a large diameter portion 17 and a small diameter portion 19 having cavities 21 and 23, respectively formed therein. The small diameter portion 19 includes an inlet passage 25 connected thereto for introduction of the flowable material into the cavity 23. The inlet passage 25 includes a flange 27 formed thereon for connecting to a source of the flowable material. Furthermore, the inlet passage 25 includes an opening 29 into the cavity 23. The inlet passage 25 is preferably located offset with respect to a plane passing through an axis of the small diameter portion 19 in order to create a vortex flow through the collection chamber. The vortex flow through the collection chamber scours the surfaces of the collection chamber and forces any flowable material therein down to the opening in the drain passage and then up and out through the drain passage.

A flange 31 is mounted at an intermediate position on the small diameter portion 19 for connecting the dip tube valve assembly 1 to the wall of a vessel or conduit (not illustrated in FIGS. 1 and 2). As is well known, the vessel or conduit would include a flange (not illustrated) for cooperating with the flange 31 formed on the small diameter portion 19 for removably securing the dip tube valve assembly to the vessel or conduit. Alternatively, the body 3 may be welded or otherwise permanently affixed into the wall of the vessel or conduit somewhere along the outside surface of the small diameter portion 19 below the inlet passage 25. There would be a smooth transition along the outside surface of the small diameter portion 19 in this case, since it would be unnecessary to provide the flange 31.

It is noted that the "large diameter" and "small diameter" character of the portions 17 and 19 are not important. The only requirement is that the portions 17 and 19 include cavities 21 and 23 of a sufficient size to fit the mechanical elements within cavity 21 and to provide sufficient space for the free flow of material within cavity 23. It is possible to make the small diameter portion 19 larger than the large diameter portion 17, depending upon the application.

Referring specifically to FIG. 1, the small diameter portion 19 may also include an insulating jacket 33 which is formed by securing a cylinder around the small diameter portion, the cylinder having an inside diameter which is larger than an outside diameter of the small diameter portion 19. A space 35 is formed between the insulating jacket 33 and the small diameter portion which can be filled with an insulating material or can merely be an air space. The insulating jacket 33 is not a required element of the present invention. Referring to FIG. 2, the dip tube valve assembly is illustrated without an insulating jacket 33. The insulating jacket is useful in applications which require thermal, electrical or other insulation to insulate the internal portion of the dip tube valve assembly from the surrounding environment. In view of this, the insulating jacket can also be thermal, electrical, magnetic and/or chemical. Furthermore, the insulation can be carried out through the use of insulating coatings or other materials of construction selected according to their properties, as well as the multiple wall construction of the present embodiment. The insulating jacket of the present invention can be made in accordance with U.S. Application Publication No. 2002-0185626A1, dated Dec. 12, 2003, which is incorporated herein by reference.

Referring again to FIG. 1, the shaft 5 according to the first embodiment of the present invention includes a main shaft portion 37 and a drain passage portion 39. The main shaft portion 37 includes a handwheel 41 mounted on an end 43 thereof. A groove 45 is formed along one side of the main shaft portion 37 which engages with a pin 47 secured to the housing top 7. The pin 47 prevents rotation of the main shaft portion 37, but allows the main shaft 37 to reciprocate with respect to the housing top 7.

The handwheel 41 includes an aperture 49 formed therein which includes threads 51 for threadably engaging threads 53 formed on an outside surface of the housing top 7. The handwheel 41 is mounted to the end 43 of the main shaft portion 37 such that no rotation occurs between the handwheel 41 and the main shaft portion 37. The attachment of the handwheel 41 to the main shaft portion 37 can be accomplished by any means which prevents rotation between the two members including press fitting, a screw, etc., all of which would be readily apparent to the ordinary artisan.

It is also noted that the present invention is not limited to the use of a handwheel; but any mechanism for causing reciprocating motion of the shaft 5 can be used. Furthermore, it is within the scope of the present invention to provide an automatic device rather than the manual handwheel illustrated.

The drain passage portion 39 of the shaft 5 is connected to the main shaft portion 37 by cooperating threads 55 and 57 respectively formed on the main shaft portion 37 and the drain passage portion 39. The drain passage portion 39 includes a shoulder 59 formed thereon for securing a diaphragm 61 between the shoulder 59 and an end 63 of the main shaft portion 37. The diaphragm 61 is secured around an outside perimeter thereof by being sandwiched between a shoulder portion 65 formed on the large diameter portion 17 and an inner cylinder 67 fitted within the cavity 21 of the large diameter portion 17. The inner cylinder 67 is held in contact with the diaphragm 61 by the flange 11 when the flanges 11 and 13 are connected to each other. The inner cylinder 67 can be removed from the large diameter portion when the flanges 11 and 13 are separated from each other. This provides for easy removal and replacement of the diaphragm 61 in the case of wear. The diaphragm seals the cavity 21 formed in the large diameter portion 17 of the housing base 9 from the small diameter portion 19, while allowing the shaft 5 to reciprocate within the housing base 9.

It is noted that an o-ring (not illustrated) can be used as an alternative to the diaphragm of FIG. 1. Furthermore, any other arrangement that provides an adequate seal between the shaft 5 and the housing base 9 can be used as well.

Referring to FIG. 2, the drain passage portion 39 also includes a drain passage 69 formed therethrough. A lower end 71 of the drain passage 69 includes a radial portion 75 which extends from a center of the drain passage portion 39 to an opening 73 formed on the outside surface of the drain passage portion 39. The opening 73 is in communication with a collection chamber 74 formed at a bottom of the cavity 23 in the small diameter portion 19 of the housing base 9 when the dip tube valve assembly is in the closed position as illustrated in FIG. 1. However, the opening 73 is in communication with an inside of the vessel or conduit (not illustrated in FIGS. 1 and 2) when the dip tube valve assembly 1 is in the open position as illustrated in FIG. 2.

The opening 73 of the drain passage 69 can be oriented offset with respect to a plane passing through the central axis of the drain passage in a similar but opposing fashion to the inlet passage so as to open into the vortexing flow. The effect of this is to sweep material down, into and then up and out of the drain passage.

It should be noted that a collection basin or well is formed at the bottom of the collection chamber 74 at the lowest point of the collection chamber 74. In applications particularly useful for sampling, it is preferable to provide the lowest point in the collection chamber 74 immediately adjacent to the opening 73 of the drain passage 69. This will ensure that the sampled material will accumulate at the opening 73 in order to enhance the removal of the material which has collected therein.

Furthermore, as best illustrated in FIG. 2, a screw portion 79 is formed on a lower end 77 of the drain passage portion 39. This screw portion 79 is for threadably receiving a sealing tip 81 thereon. The sealing tip 81 is for sealing an orifice 83 formed at a lower end 85 of the small diameter portion 19 of the housing base 9 and includes a flexible outer covering 89 and a rigid internal portion 91. The rigid internal portion 91 includes threads 92 formed therein for cooperating with the screw portion 79. In addition, the lower end 85 of the small diameter portion 19 includes an internal shoulder 87 formed thereon for engaging with the flexible outer covering 89 of the sealing tip 81 in order to provide a sufficient seal therebetween.

It is noted that the sealing tip need not be secured in the manner illustrated in FIG. 1, but may be secured in any other manner that provides a sufficient connection between the drain passage portion 39 and the sealing tip 81. For example, a nut may be threadably attached to the screw portion 79 from a lower surface of the sealing tip 81. Furthermore, the seal between the orifice and the bottom of the shaft 5 need not be performed with the sealing tip 81 illustrated in FIGS. 1 and 2. It is only necessary that the shaft 5 include a sealing tip that can be brought into cooperation with the orifice in order to form a seal therebetween. This can be accomplished by a soft flexible seal as in FIGS. 1 and 2, a metal-to-metal seal, or other sealing device.

Referring again to FIG. 1, the main shaft portion 37 includes a drain passage 93 formed therethrough. The drain passage 93 communicates the drain passage 69 in the drain passage portion 39 to a drain outlet 95. The drain outlet 95 can be welded to the main shaft portion 37 or can include threads (not illustrated) for engaging with threads (not illustrated) formed in the main shaft portion 37. The drain outlet 95 includes a flange 97 formed thereon for connecting the drain outlet 95 to other equipment downstream for processing the flowable material supplied therethrough. The drain outlet 95 extends through an aperture 96 formed in the large diameter portion 17. The aperture 96 is elongated in the longitudinal direction of the body 3 in order to provide for reciprocating movement of the drain outlet 95 along with the reciprocating movement of the shaft 5. It is noted that the aperture 96 need only be large enough to allow for movement of the drain outlet 95.

Alternatively, the drain outlet 95 can be attached directly to the large diameter portion 17. A flexible tube can then attach the inside of the drain outlet 95 to the drain passage 93 formed in the main shaft portion 37. The tube can be coiled in the cavity 21 in order to provide sufficient space to reciprocate the shaft 5.

The operation of the first embodiment of the present invention will now be described. Referring to FIG. 1, the dip tube valve assembly 1 is in the closed position and ready for a feeding or a sampling process to take place. The sealing tip 81 is positioned in contact with the internal shoulder 87 of the small diameter portion 19, forming a seal therebetween.

The valve is opened by rotating the handwheel 41 to move the shaft 5 in a longitudinal direction to position the sealing tip in the position illustrated in FIG. 2. If a feeding process is desired, the flowable material is fed through the inlet passage 25, through the collection chamber 74, through the orifice 83 and into the vessel or conduit (not illustrated in FIGS. 1 and 2). If a sampling process is desired, the inlet passage 25 is closed upstream from the valve. This causes a vapor lock which inhibits back-filling into the cavity 23 of the small diameter portion 19 and causes the sampled material to flow up and out of the drain passage 69, rather than the inlet passage 25. Once the material is completely fed into the vessel or conduit or the sample is removed from the vessel or conduit, the valve is closed by rotating the handwheel 41 in an opposite direction to move the shaft 5 to the position illustrated in FIG. 1. Any excess feeding or sampled material will drain down into the collection chamber, and due to the location of the opening 73 of the drain passage 69, the material will collect at the bottom of the collection chamber adjacent to the opening 73 of the drain passage 69.

Some processes or some steps of processes are carried out at lower pressures than ambient. As a result, a vacuum may be necessary to draw the sample up and out of the vessel or conduit and through the drain passage 69.

If a sampling process was performed, it may be desirable to remove any of the remaining sample material which has collected adjacent the opening 73. This is accomplished by feeding a flowable material, such as a gas, through the inlet passage 25. Since the axis of the inlet passage 25 is oriented non-parallel to a plane passing through the major diameter of the body 3 of the dip tube valve assembly 1, the flowable material creates a vortex flow through the cavity 23 to the opening 73 and through the drain passage 69. The vortex flow scours the surfaces of the inlet passage 25, cavity 23 and drain passage 69 in order to remove the remaining sample therefrom.

If it is desired to clean or sterilize the dip tube valve assembly, a cleaning or sterilizing solution can be fed through the inlet passage 25 and out of the drain passage 69. If this cleaning or sterilizing solution is a liquid and it is desired to remove remaining solution from the collection chamber, it is possible to force the remaining solution therefrom by providing a flowable material through the inlet 25 in the same manner as above.

Figure 3:
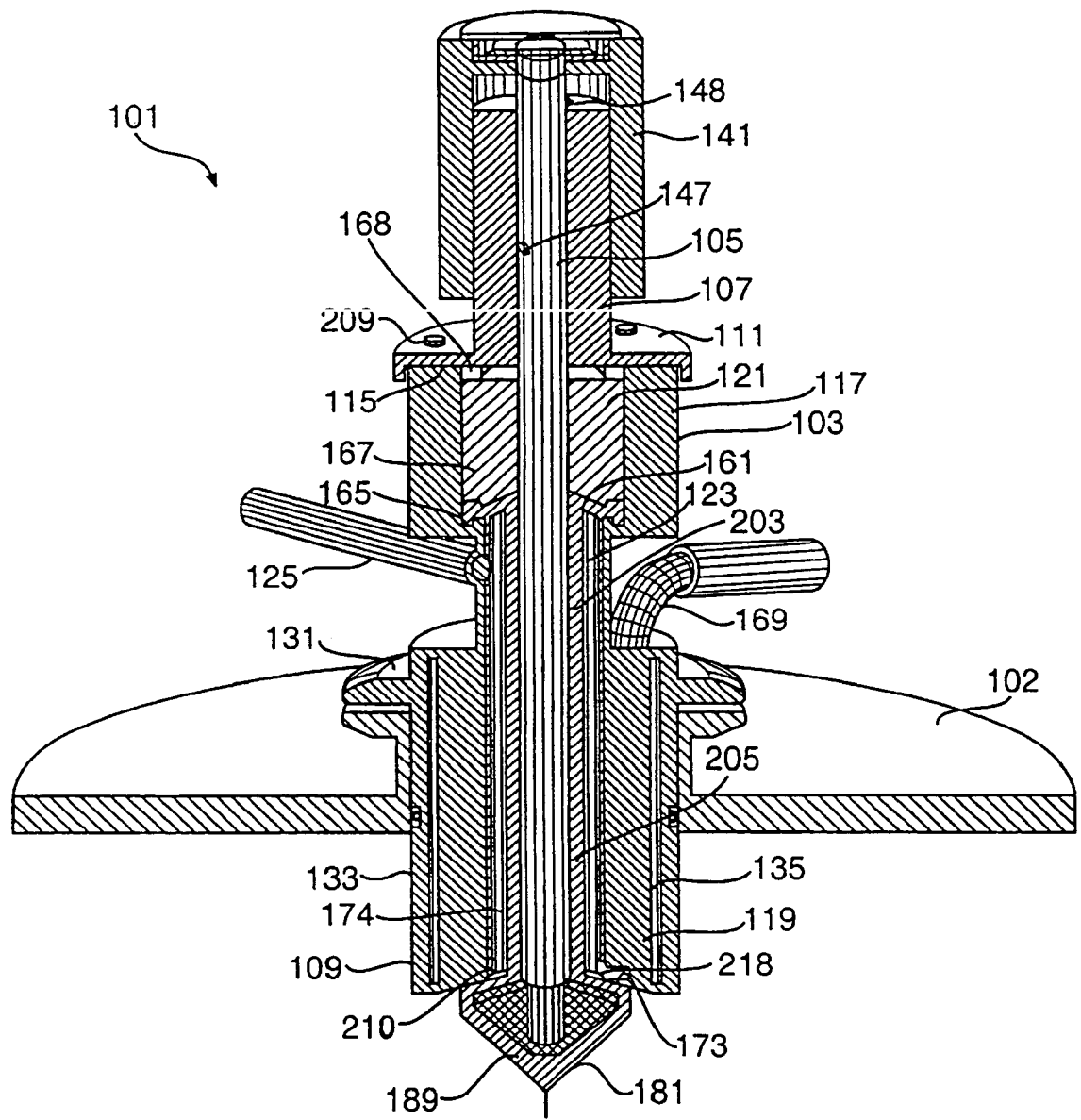
FIG. 3 is a cross-section of the dip tube valve assembly according to a second embodiment of the present invention, wherein the valve is illustrated in a closed position.
Figure 4:
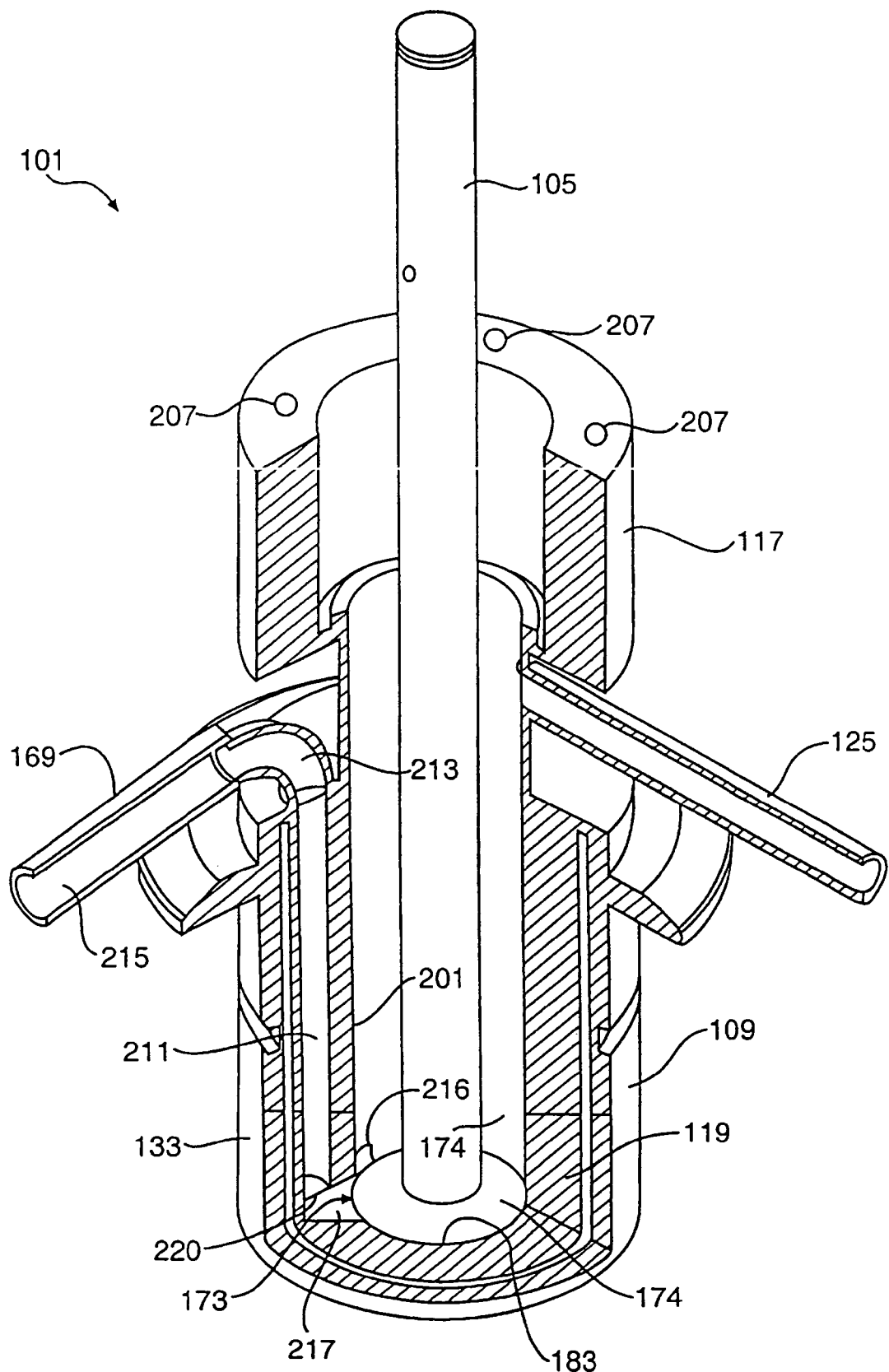
FIG. 4 is a cross-section of the second embodiment of the present invention through the drain passage and the inlet passage.
Figure 5:
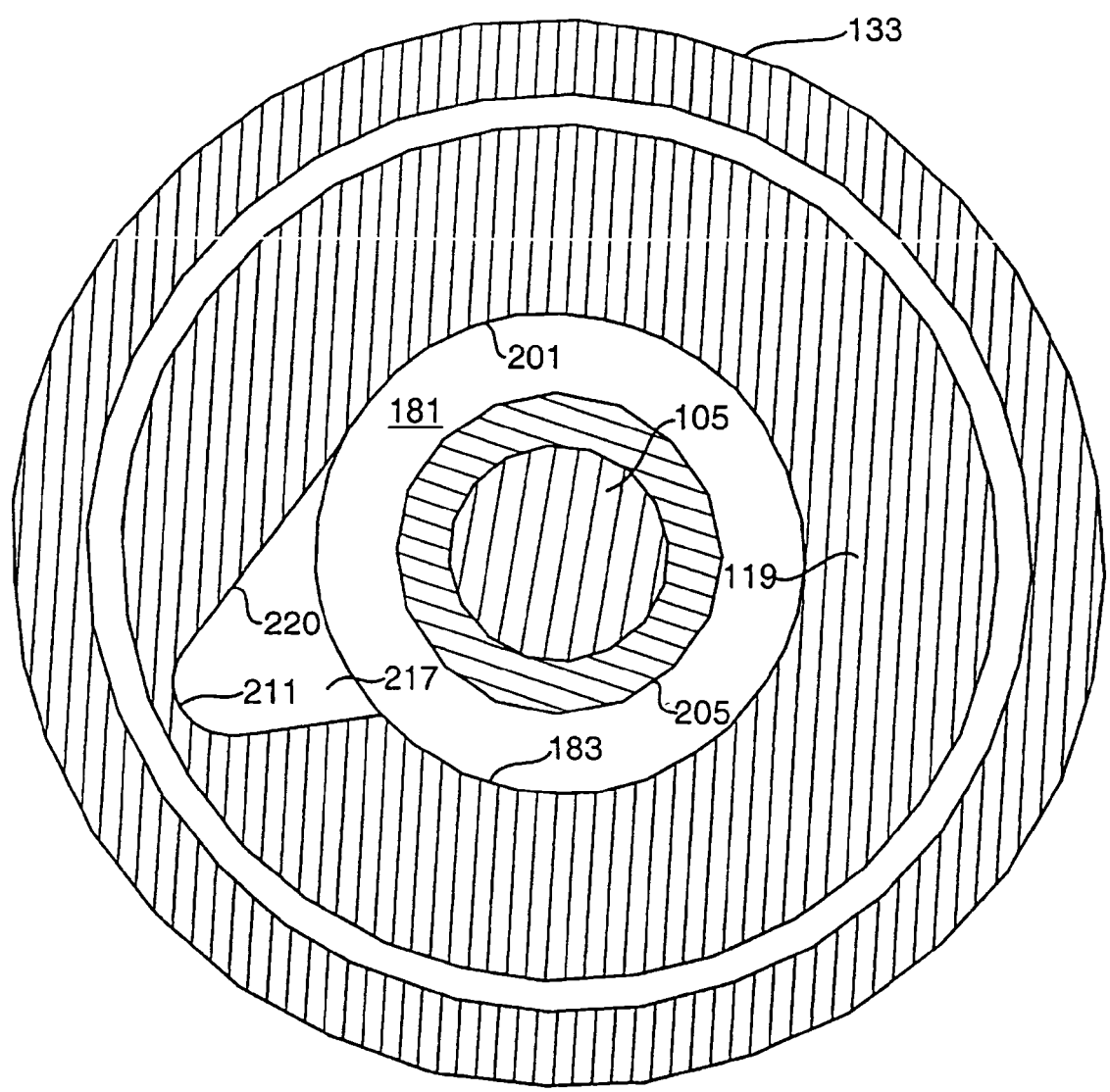
FIG. 5 is a cross-section through the lower horizontal section of the drain passage.

A second embodiment of the present invention will now be described with reference to FIGS. 3-5. FIG. 3 is a cross-section of the dip tube valve assembly according to the second embodiment, wherein the valve is illustrated in the closed position. FIG. 4 is a cross-section of the second embodiment through the drain passage and the inlet passage. FIG. 4 is illustrated with several of the elements removed, including the housing top, sealing tip and handwheel, for ease of understanding. FIG. 5 is a cross-section through the lower horizontal section of the drain passage of FIGS. 4 and 5.

The second embodiment of the present invention operates substantially the same as the first embodiment; however, the drain passage is located in the body of the dip tube valve assembly rather than in the reciprocating shaft. Elements which are the same as or similar to the first embodiment have been identified by the same reference numerals with 100 added thereto.

Referring to FIG. 3, the dip tube valve assembly 101 is secured to a vessel or conduit 102 through a flange 131 formed on the small diameter portion 119. As noted above, a conventional vessel or conduit typically includes a flange formed thereon for easy installation of the dip tube valve assembly 101 of the present invention.

Referring to FIGS. 3 and 4, the dip tube valve assembly 101 includes a drain passage 169 formed in the small diameter portion 119 of the housing base 109. The opening 173 of the drain passage 169 is formed on an inside wall 201 of the small diameter portion 119 adjacent to the orifice 183. Furthermore, the inlet passage 125 is formed in the small diameter portion 119 at a location above the location of the opening 173.

Referring to FIG. 3, the shaft 105 is a solid shaft which extends from the handwheel 141 to the sealing tip 181. It is unnecessary to provide multiple pieces to the shaft 105, since there is no passageway formed inside the shaft 105 as in the first embodiment. Forming the drain passage in the housing base, rather than in the shaft provides the advantage of manufacturing the shaft with a smaller diameter than the shaft of the first embodiment. However, as can be readily understood, it is necessary to make the thickness of the wall of the small diameter portion 119 in the second embodiment larger in order to accommodate the drain passage 169.

The second embodiment illustrated in FIG. 3 also includes a one-piece member 203 that acts as the diaphragm 61 and the flexible outer covering 89 of the first embodiment. Specifically, the one-piece member 203 includes a diaphragm portion 161 and a flexible outer covering 189. In addition, the one-piece member 203 includes a connecting portion 205 which connects the diaphragm portion 161 to the flexible outer covering 189. The one-piece member 203 of the second embodiment is advantageous, since only one piece is necessary to seal the orifice 183 and the end of the small diameter portion 119 adjacent to the large diameter portion 117. However, it will be readily apparent that the diaphragm 61 and the flexible outer covering 89 of the first embodiment can be substituted in the second embodiment and the one-piece member 203 of the second embodiment can be used in the first embodiment.

FIG. 3 also includes an alternative way to secure the housing top 107 to the housing base 109. A flange 111 is formed on the lower end of the housing top 107. Furthermore, a plurality of threaded holes 207 (see FIG. 4) are formed in the upper surface of the housing base 109. The flange 111 also includes holes (not illustrated) corresponding to the threaded holes 207 in the housing base 109. A plurality of screw 209 are fitted in the threaded holes 207 to fasten the flange 111 to the housing base 109. A gasket 115 may also be included between the flange 111 and the housing base 109 for proper sealing. Gasket 115 is not always necessary; however, it does help to form a second seal with the environment. It is noted that the above alternative can also be used in the first embodiment and the flanges and clamp of the first embodiment can be used in the second embodiment.

In FIG. 3, an alternative arrangement is illustrated to hold the diaphragm portion 161 in contact with the shoulder portion 165 of the large diameter portion 117. A cylindrical member 167 has an aperture formed therein for receiving the shaft 105 and a bottom surface having a conical shape corresponding to the upper surface of the diaphragm portion 161. Furthermore, a cylindrical member 168 is located above the cylindrical member 167 in order to force the diaphragm portion into contact with the shoulder portion 165 when the housing top 107 is connected to the housing base 109. It should be noted that the cylindrical member 168 is not required, since the flange 111 of the housing top 107 can directly contact the cylindrical member 167 to hold the diaphragm portion 161 in place.

As an alternative to preventing rotation of the shaft 105 with respect to the housing top 107, FIG. 3 illustrates a pin 147 fixed to the shaft 105 for engaging a keyway 148 formed in the housing top 107. Specifically, an aperture is formed extending through the shaft 105. This aperture receives pin 147 such that the pin extends outwardly from the shaft 105 on opposite sides of the shaft 105 (only one side of the pin 147 is illustrated). The ends of the pin engage in keyways 148 formed in the housing top 107 (only one keyway is illustrated). This allows the shaft 105 to reciprocate, while preventing the shaft from rotating when the handwheel 141 is rotated with respect to the housing top 107.

FIGS. 3 and 4 also illustrate the use of an insulating jacket 133 which forms a space between the small diameter portion 119 and an inside of the insulation jacket 133 in order to insulate the flowable material within the dip tube valve assembly or to insulate the process from the repeated hot steam resterilization of the dip tube valve assembly, usually performed after each sampling or feeding episode. As noted above, the insulation jacket 133 is only necessary if used in an environment that requires that the flowable material be insulated.

Referring to FIG. 4, the drain passage 169 is illustrated in cross-section. The drain passage 169 includes a vertical section 211, a curved portion 213, an upper horizontal section 215 and a lower horizontal section 217. It should be noted that the terms vertical and horizontal are used only for the purposes of description, since the dip tube valve assembly of the present invention is not required to be used in the position illustrated in the drawings. Furthermore, the upper horizontal section need not be horizontal, since it is preferable to have this section tilt downwardly in order to allow for material to drain out of the inside of the dip tube valve assembly 1 after the flowable material is turned off. The horizontal section 215 is attachable to downstream equipment in order to further process the flowable material. The lower horizontal section is formed by machining out the inside wall 201 of the small diameter portion 119. A generally square section of the inside wall 201 is cut out from the edge of the orifice 183 toward the vertical section 211 as illustrated in FIG. 3. The lower surface of the lower horizontal section 217 is generally even with or slightly angled downwardly from the edge of the orifice 183. Furthermore, an additional portion 216 of the inside wall 201 is cut out in order to form a smooth transition from the inner wall 201 to the drain passage 169 and to ensure that the opening 173 of the drain passage 169 is sufficiently wide. Accordingly, when the flowable material is fed through the inlet passage 125 to the opening 173 of the drain passage 169, the flowable material and any remaining feeding material, sampled material, or cleaning or sterilizing solution are thoroughly swept out of the drain passage 169.

In the second embodiment of the present invention, it is possible to prevent any pooling of the material therein other than immediately adjacent to the opening 173. Furthermore, since the lower horizontal section is formed generally even with the edge of the orifice 183, and actually may slope downwardly from the orifice 183, it is possible to provide for the pooling to occur in the lower horizontal section 217 itself, since the lower horizontal section 217 is lower than or even with the bottom of the collection chamber 174 in this embodiment. In the case where the lower horizontal section 217 is lower than the bottom of the collection chamber 174, the lower horizontal section 217 forms the collection well, since the lower horizontal section 217 is the lowest point within the collection chamber 174.

Referring to FIG. 3, since the sealing tip 181 is bulged upwardly at 210 due to the flexing of the flexible outer covering 189 when in the sealed position, any material remaining in the collection chamber 174 flows downwardly and into the horizontal section 217 of the drain passage 169.

The embodiment of FIGS. 3 and 4 is superior with regard to drainage of material being fed or sampled, even when the dip tube valve assembly is located such that the longitudinal direction of the body 103 is located nearly horizontal. Furthermore, this embodiment is superior with regard to cleaning of the interior between feeding and sampling episodes.

The above advantages of this embodiment can be particularly realized if the drain passage 169 is located very close to the collection chamber 174, i.e., the wall between the drain passage 169 and the collection chamber 174 is made very thin and the opening 173 is made as small as possible. However, it should be noted that the opening 173 should not be made smaller than the drain passage 169, since this would cause drain passage 169 to form a low energy "settling" zone with respect to the opening 173 and other possible areas.

Referring again to FIGS. 4 and 5, the drain passage 169 and the collection chamber 174 are connected by the opening 173 which includes the lower horizontal section 217. The lower horizontal section 217 includes a wall 218 having a lower margin 220 which is co-linear with a tangent to the inside surface 201 of the collection chamber 174 at the orifice 183. Furthermore, the lower margin 220 is co-linear with a tangent to the vertical section 211 of the drain passage 169. The tangents to the inside surface 201 and the vertical section 211 are coplanar with the bottom of the lower horizontal section 217. Furthermore, the lower margin 220 of the wall 218 is coplanar with a plane passing through the radial seal between the orifice 183 and the sealing tip 181. This configuration will make the dip tube valve assembly 101 the most effective at concentrating material for the purpose of cleaning and flushing near the opening 173 of the drain passage 169 at all angles of installation from the vertical down to near-horizontal, whether the device is used for sampling or feeding.

Referring specifically to FIG. 5, the lower margin 220 of the wall 218 is clearly illustrated extending from the inside wall 201 to the vertical section 211 of the drain passage 169. The bulging portion 210 of the sealing tip 181 is raised with respect to the bottom of the lower horizontal section 217. Accordingly, the material in the collection chamber 174 flows from the sealing tip 181 and into the lower horizontal section 217.

The above aspects of the embodiment of FIGS. 3-5 can be better understood with the following explanation. If a flushing gas is introduced radially at the top of the collection chamber 174, the vortexing flow created will tend to scour the surfaces of the interior of the body 103 and carry the material down the inside wall 201, including the lower outside margin of the inside wall 201 where it is coplanar with the lower outside wall of the vertical section 211 of the drain passage 169 and the lower margin 220. Because of this, the material being carried along by the flushing gas will tend to flow into the drain passage and up and out of the body 103.

Since the drain passage in this embodiment is located radially outwardly from the collection chamber 174, the centripetal force caused by the vortexing flow naturally causes the material to be flushed to move outwardly toward the drain opening 173.

The drainage of the body 103 will only be most enhanced if it is installed at angles that tilt the body 103 back from the vertical on an axis formed by the lower margin 220 of the wall 218. Specifically, if the body 103 is installed at an angle less than the vertical, gravity will tend to collect the material along the lower margin 220 of the wall 218, i.e., at the intersection of the wall 218 and the bottom wall of the lower horizontal section 217.

Figure 6:
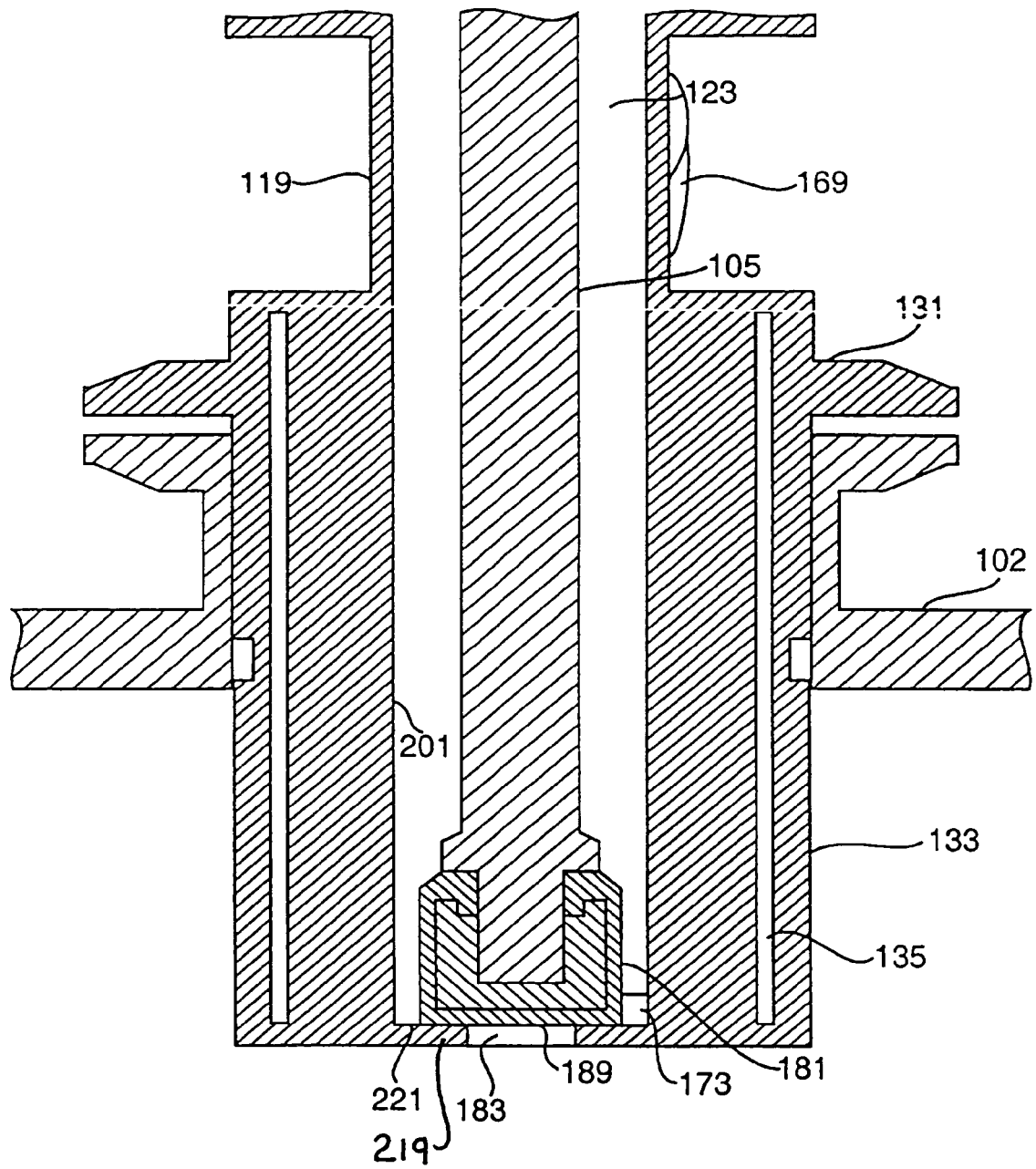
FIG. 6 is a cross-section of an alternative arrangement of the sealing tip of the present invention.

An alternative arrangement of the sealing tip of the present invention will now be described with reference to FIG. 6. The embodiment of FIG. 6 is generally the same as the embodiment of FIGS. 3 and 4, except for the fact that the shaft 105 is held in compression, rather than in tension to seal the orifice 183. Furthermore, the sealing tip 181 is similar to the embodiment illustrated in FIGS. 1 and 2. The same reference numerals have been used in the embodiment of FIG. 6 that have been used in the embodiment of FIGS. 3 and 4.

Referring to FIG. 6, the sealing tip 181 is located in the closed position, wherein the flexible outer covering 189 is located in sealing contact with an inner shoulder 219 to seal the orifice 183. The inner shoulder 219 is formed by a wall extending inwardly from the inside wall 201 of the small diameter portion 119. In order to open the orifice 183, the shaft 105 is moved upwardly in FIG. 6 to move the sealing tip 181 away from the inner shoulder 219.

The inner shoulder 219 is illustrated in FIG. 6 such that the upper surface 221 is generally horizontal. However, the upper surface 221 can be sloped either upwardly or downwardly, depending upon the application. If the upper surface 221 is sloped upwardly, the embodiment of FIG. 6 would be more advantageous if used as a sampling device, since the remaining sampled material would settle at the opening 173. If the upper surface 221 is sloped downwardly as a feeder/innoculator, since the material being fed would drain down into the orifice 183.

With regard to the insulating jacket 133 in FIG. 6, as noted above, the insulating jacket 133 is only necessary in applications that require insulation. Further to this, the space 135 formed by the insulating jacket is illustrated in the form of a cylinder. However, this space 135 can also include a horizontal opening extending inwardly from the space 135 toward the orifice 183 in order to further insulate the process from the dip tube valve assembly 101. A horizontal space would be most useful in pharmaceutical or food applications where the repeated sterilizing from steam can heat up the material in the vessel above a desired temperature.

It should be noted that the above embodiments in FIGS. 1-5 are illustrated as being formed from concentric cylindrical members secured to each other such that the shafts 5, 105 are located at the center of the cylinders. However, it is possible to form the body 3, 103 of the dip tube valve assembly 1, 101 of asymmetric or irregular shaped pieces. For example, in the embodiment of FIG. 4, it is possible to narrow the wall of the small diameter portion 119 on the side opposite to the drain passage 169 such that the shaft 105 is located more toward the side opposite to the drain passage 169. This will provide a dip tube valve assembly having a smaller cross-sectional area.

Figure 7:
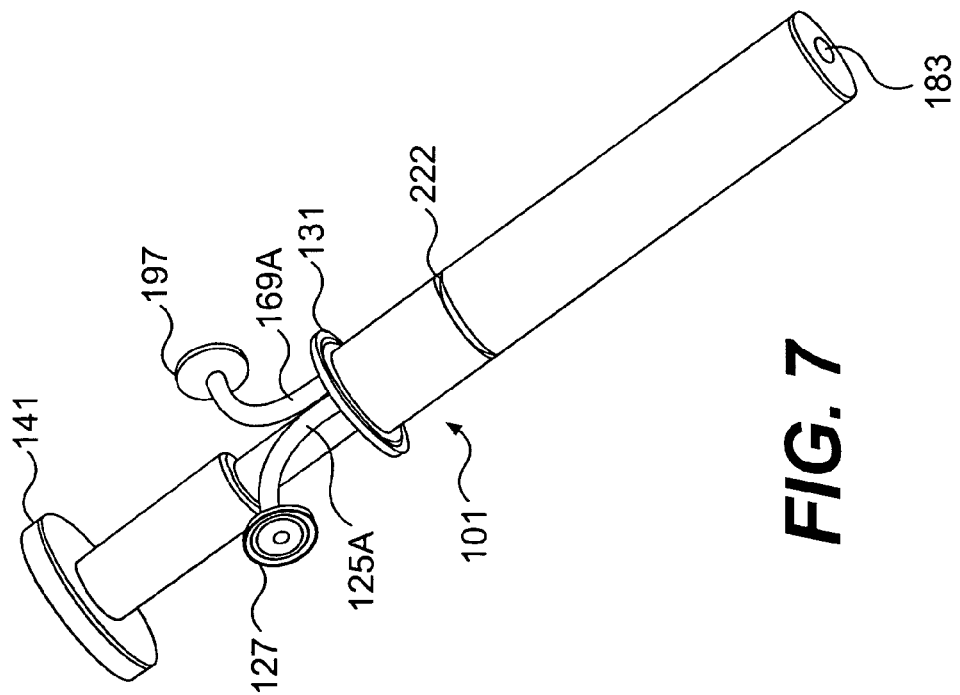
FIG. 7 is a perspective view of a third embodiment of the present invention.
Figure 8A:
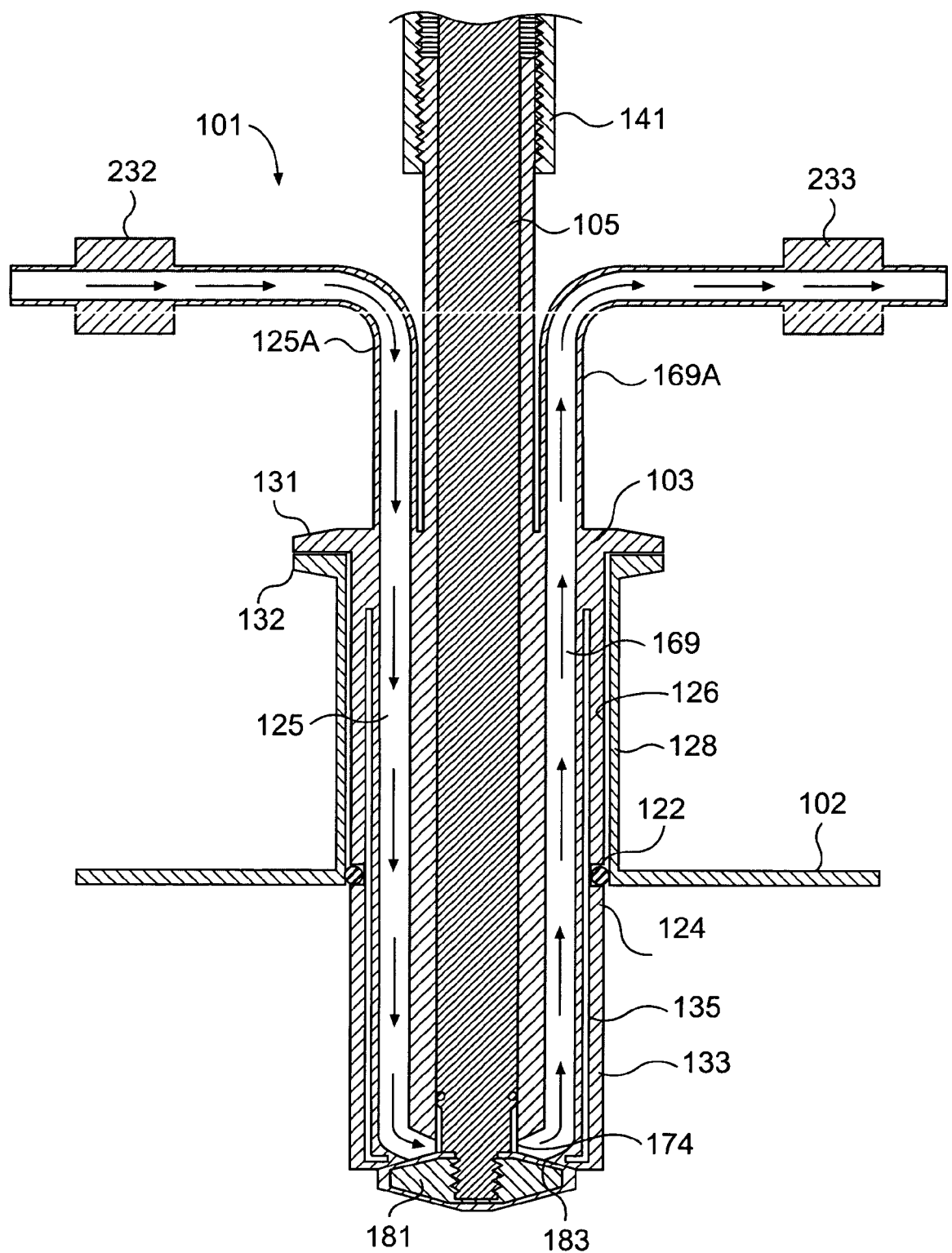
FIGS. 8A and 8B are cross-sectional views through the inlet and drain passages of FIG. 7.
Figure 8B:
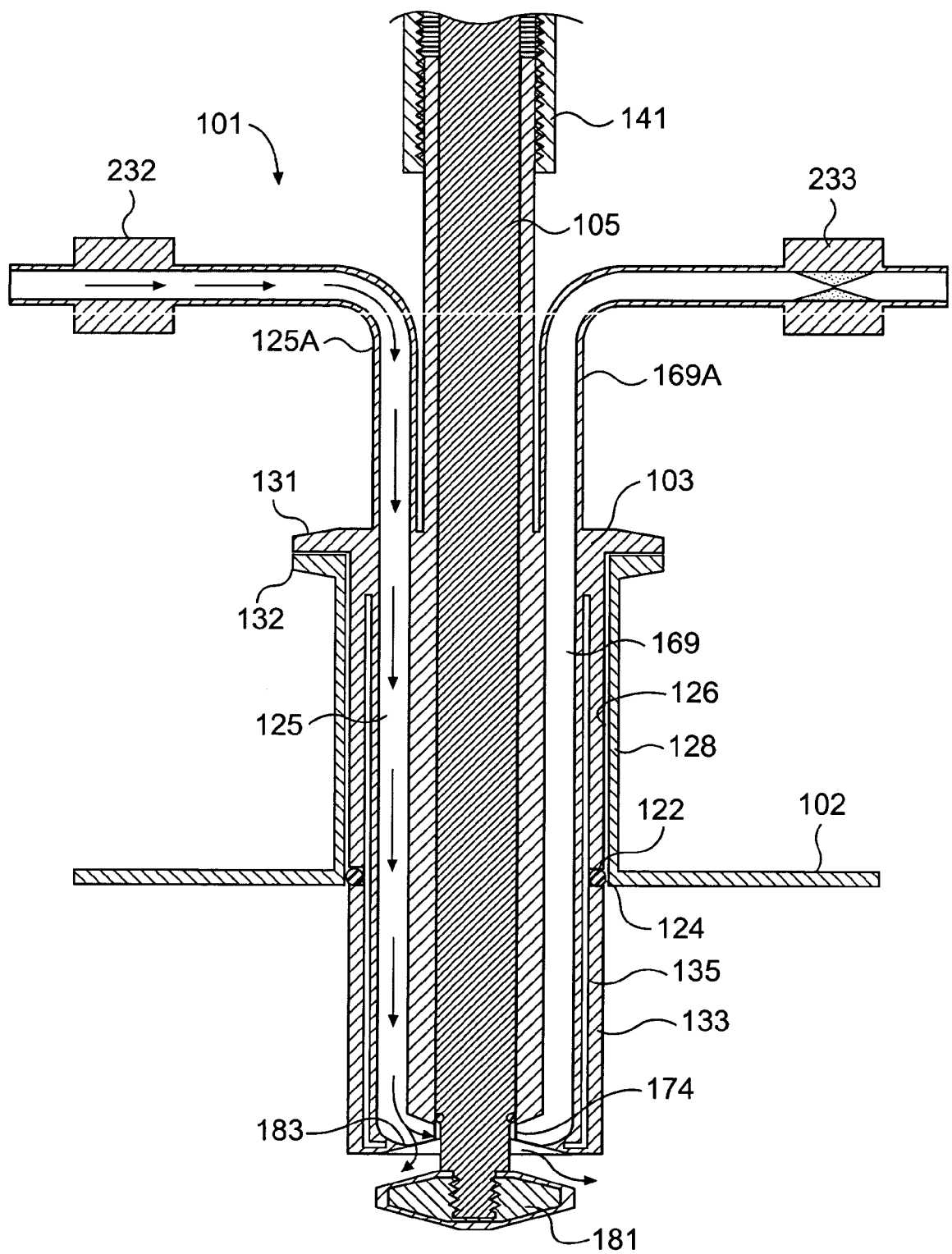

Referring to FIGS. 7, 8A and 8B, a third embodiment of the present invention is illustrated. It should be noted that the same reference numerals as the embodiment of FIGS. 3-5 have been used for the same or similar elements where possible. In FIGS. 7, 8A and 8B, as well as the later described embodiments of the present invention, the collection chamber 174 has been decreased in size substantially when compared with the first and second embodiments of the present invention. The reduced collection chamber 174 minimizes the internal valve volume and increases directed flow through the collection chamber 174 and past the sealing tip 181 to enhance the ability of the dip tube valve assembly 101 to be cleaned and fully flushed and dried between uses.

Referring to FIG. 7, an external view of the dip tube valve assembly 101 is illustrated. As in the previous embodiments, a resealable orifice 183 is provided at one end of the body 103. An o-ring groove 122 is designed to receive an o-ring 124 to form a seal between the body 103 and the inside circumferential wall 126 of the port 128 in the vessel or conduit 102 (See FIG. 8A).

It should be noted that the seal between the body 103 and the vessel or conduit 102 can be accomplished in other ways as well. For example, a gasket in combination with the flange 131 can be used. By capturing the gasket between the flange 131 and a mating opposing flange 132 on the vessel or conduit 102, a seal will also be formed. As mentioned above, seals formed at the location of the groove 122 and the flange 131 are two examples of how the body 103 of the dip tube valve assembly 101 may be sealed in a vessel or conduit 102. However, it should be understood that both of the above-described seals may be used in combination to provide a redundant or multiple seal.

Mating and securing the flange 131 into an opposing flange 132 of the port 128 in the vessel or conduit 102 also serves as one method to anchor the valve body 103 into the vessel or conduit 102. However, many other methods for removably anchoring the device would be obvious to one knowledgeable in the art as would the possibility of permanently affixing the valve body 103 into the wall of the vessel or conduit 102. The act of welding, gluing or otherwise permanently affixing the valve body 103 into a wall of the vessel of conduit 102 may also eliminate the space between the valve body 103 and the vessel or conduit 102, thereby also eliminating the need to provide a seal in this space. Of course, this permanent attachment of the valve body to the wall of the vessel or conduit could be used in any of the previous embodiments or any of the embodiments which will be described below.

Referring again to FIG. 7, a handwheel 141 is illustrated extending out through the top of the flange 131. The handwheel 141 operates in the same manner as the previous embodiments and therefore will not be further described. In addition, FIGS. 8A and 8B illustrate inlet passage 125 and drain passage 169. The inlet and drain passages 125 and 169 include external tube extensions 125A and 169A extending above the flange 131. In FIG. 7, the external tube extensions 125A and 169A of the inlet and drain passages 125 and 169 terminate at flanges 127 and 197, respectively, for connecting the inlet and drain passages 125 and 169 to a supply source (not shown) and a drain (not shown), respectively. As will be understood to one having ordinary skill in the art, the supply of material and the drain can include piping and valves in order to control the various operations of dip tube valve assembly 101 of the present invention.

Referring to FIGS. 8A and 8B, the external tube extensions 125A and 169A are illustrated hard piped directly to external supply and drain lines. This construction eliminates the need for the flanges 127 and 197 of FIG. 1. The supply and drain lines for the dip tube valve assembly 101 may also be equipped with flow control valves 232 and 233, respectively, to control flow through the internal valve passages of the dip tube valve assembly 101. The flow control valves in FIG. 7 would be located upstream and downstream of the flanges 127 and 197, respectively.

Referring to FIGS. 8A and 8B, a description of the operation of the third embodiment of the present invention will be described. In FIG. 8A, the sealing tip 181 is illustrated in the closed position and the flow control valves 232 and 233 are in the open position. With this orientation, it is possible to supply gas or liquid through the inlet passage 125, into the collection chamber 174 and out of the drain passage 169 as indicated by the arrows in the figure. Due to the reduced size of the collection chamber 174, the efficiency of scouring and flushing of the collection chamber 174 is improved substantially when compared with previous embodiments of the present invention.

FIG. 8A illustrates the dip tube valve assembly in the closed condition with material flowing from the supply side down to the sealing tip 181 and back up and out the drain side. However, it should be noted that the flow direction could also be reversed. In fact, during some cleaning cycles, the supply and the drain sides might be connected to a pump, creating a self-contained high flow circuit to clean the dip tube valve assembly 101. The pumping flow direction may also be reversed from time to time to further enhance cleaning activities. In any case, the direction of flow through the dip tube valve assembly 101 while the sealing tip 181 is closed allows it to be cleaned or recleaned while installed in an on-going process without affecting the process. Furthermore, it allows the dip tube valve assembly 101, to be used as a bypass when material supply to or drainage from the process is not desired.

FIG. 8B illustrates the dip tube valve assembly in the opened condition with the sealing tip 181 being out of sealing contact with the orifice 183. The flow control valve 232 is open and the flow control valve 233 is closed. Accordingly, material can be supplied through the inlet passage 125, through the collection chamber 174, and into the process within the vessel or conduit 102. As discussed above, supply could also be accomplished through the drain passage 169 as well or through both passages simultaneously or alternately. Capturing material from the process, likewise, could be accomplished through either the supply or drain passages, through both at the same time or in alternating fashion. It is merely necessary to control the flow control valves 232 and 233 and the valves and piping upstream or downstream from the process to supply material to or from the process.

It should be noted that while only two passages are shown in FIGS. 7, 8A and 8B, the dip tube valve assembly 101 could have additional supply and drain passages, each of which could be fitted with flanges or their own flow control valves. As will be discussed later, additional passages may be constructed that serve to interconnect between the various inlet and drain passages, serving as bypasses through the internal collection chamber 174 or other portions of the body 103. Flow through the additional passages may also be controlled by additional valves connected to the dip tube valve assembly 101. In addition, while the additional valves may be attached onto external extensions of the dip tube valve assembly 101, the additional passages as well as portions of the additional valve bodies may be formed or machined into the body 103 of the dip tube valve assembly 101. This allows the entire dip tube valve assembly 101 to be made more compact, efficient and less expensive to build. The above will become more clear upon a review of the description of FIG. 9 below.

Figure 9:
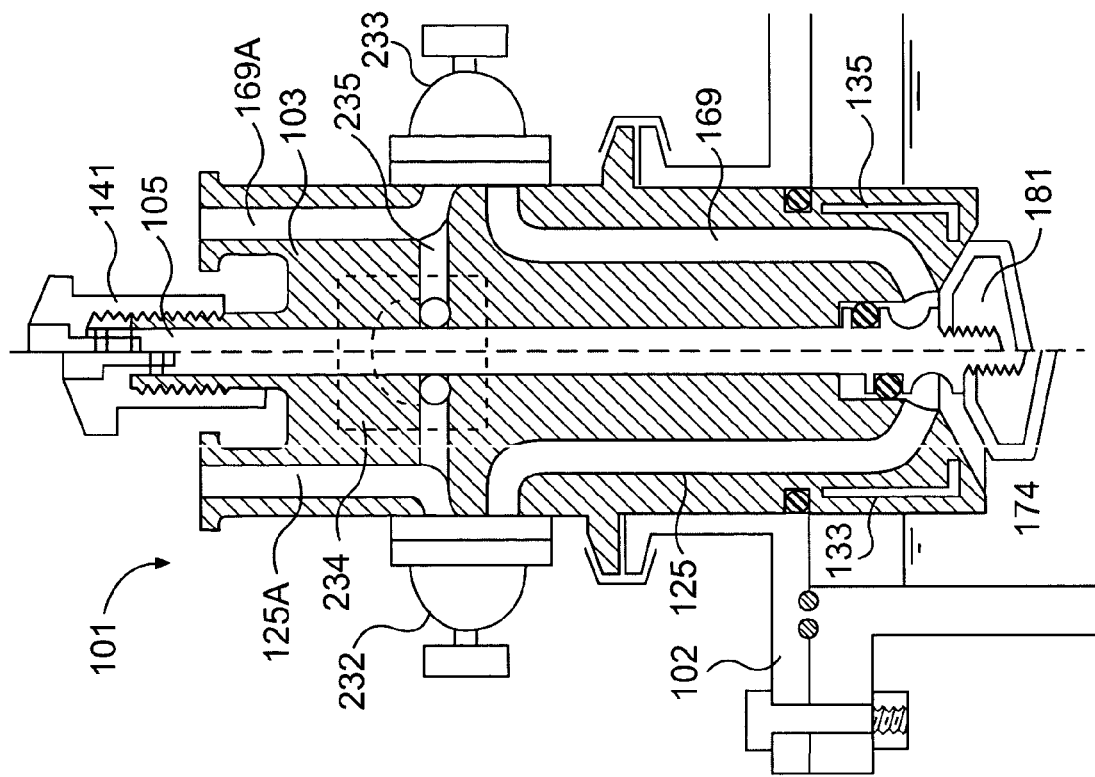
FIG. 9 is a cross-sectional explanatory view of a fourth embodiment of the present invention.

Referring to FIG. 9, a cross-section according to a fourth embodiment of the present invention will be described. Specifically, FIG. 9 a diagrammatic illustration expanded to show how many of the above-mentioned components may be combined into one dip tube valve assembly 101. In FIG. 9, the left half of the dip tube valve assembly 101 is shown in the opened condition, while the right half is shown in the closed condition. In addition, flow through the inlet passage 125 and the drain passage 169 flows through control valves 232 and 233, which are machined into the body 103 of the dip tube valve assembly 101. A bypass passage 235 is also formed in the body 103. The bypass passage 235 connects the inlet extension 125A to the drain extension 169A at a position upstream of the flow control valves 232 and 233. A third flow control valve 234 (illustrated in hidden lines) is machined on the back of the body 103. As will be understood to one having ordinary skill in the art, the control valves 232, 233 and 234 can be operated to divert flow through the bypass passage 235 instead of through the inlet passage 125, the collection chamber 174 and the drain passage 169 (or a reverse of the above). Specifically, closing the flow control valves 232 and 233 and opening the flow control valve 234 will allow flow through the bypass passage 235 to allow cleaning of the passages upstream and downstream of the supply and drain passages 125 and 169, respectively. A valve design with such a capability would be advantageous, for instance, in cases where it is desirable to have redundant seals between the process within the vessel or conduit 102 and the external supply and drain.

In FIG. 9, when the dip tube valve assembly 101 is in the closed position (see the right side of FIG. 9) with the sealing tip 181 closing the orifice 183, flow through the body 103 can be directed from the supply through the inlet extension 125A, the flow control valve 232, the inlet passage 125, the collection chamber 174, the drain passage 169, the flow control valve 233 and the drain extension 169A to the drain. As should be understood, the flow control valves 232, 233 and 234 must be controlled along with any additional valves upstream and downstream from the dip tube valve assembly 101 to direct flow in this manner. As an alternative, flow could be a reverse of the above described flow.

As mentioned above, by closing the flow control valves 232 and 233 and opening the flow control valve 234, flow can be directed from the supply through the inlet extension 125A, the flow control valve 232, the bypass passage 235, the flow control valve 233 and the drain extension 169A to the drain. Flow can also be the reverse of the above. Finally, with the sealing tip in the open position (see the left side of FIG. 9), flow can be directed through each of the inlet passage 125 and 169 and through the collection chamber 174 in order to supply material to or remove material from the process within the vessel or conduit 102.

It should be noted that although not illustrated, the flow control valve 234 could also be connected to an additional inlet/drain passage in order to supply or remove material through an additional inlet/drain extension. In addition, additional flow control valves and inlet/drain passages can be added, depending on the application.

FIGS. 8A, 8B and 9 all illustrate a dip tube valve assembly 101 with an axial bore fitted with a valve actuating rod or shaft 105 connected to a sealing tip 181 that seals the orifice 183 on an external annular surface about the orifice. The shaft 105 is fitted on an outer circumference with a single annular o-ring groove 122 and o-ring 124 that seals with a mating inner circumferential wall of the body 103 at a point adjacent to the collection chamber 174. The seal formed by the o-ring 124 and the body 103 separates the moving elements of the dip tube valve assembly 101 from the collection chamber 174. While the seal is shown as an o-ring groove 122 and o-ring 124 combination, it should be noted that this sealing arrangement could be any appropriate sealing arrangement. O-ring seals and packing seals are preferable in high pressure applications where a high degree of segregation of the moving valve elements from the flow through the dip tube valve assembly 101 are desired, while diaphragm sealing arrangements are preferred where absolute (or near absolute) segregation is desired but usage can generally be limited to lower pressure applications.

Figure 10:
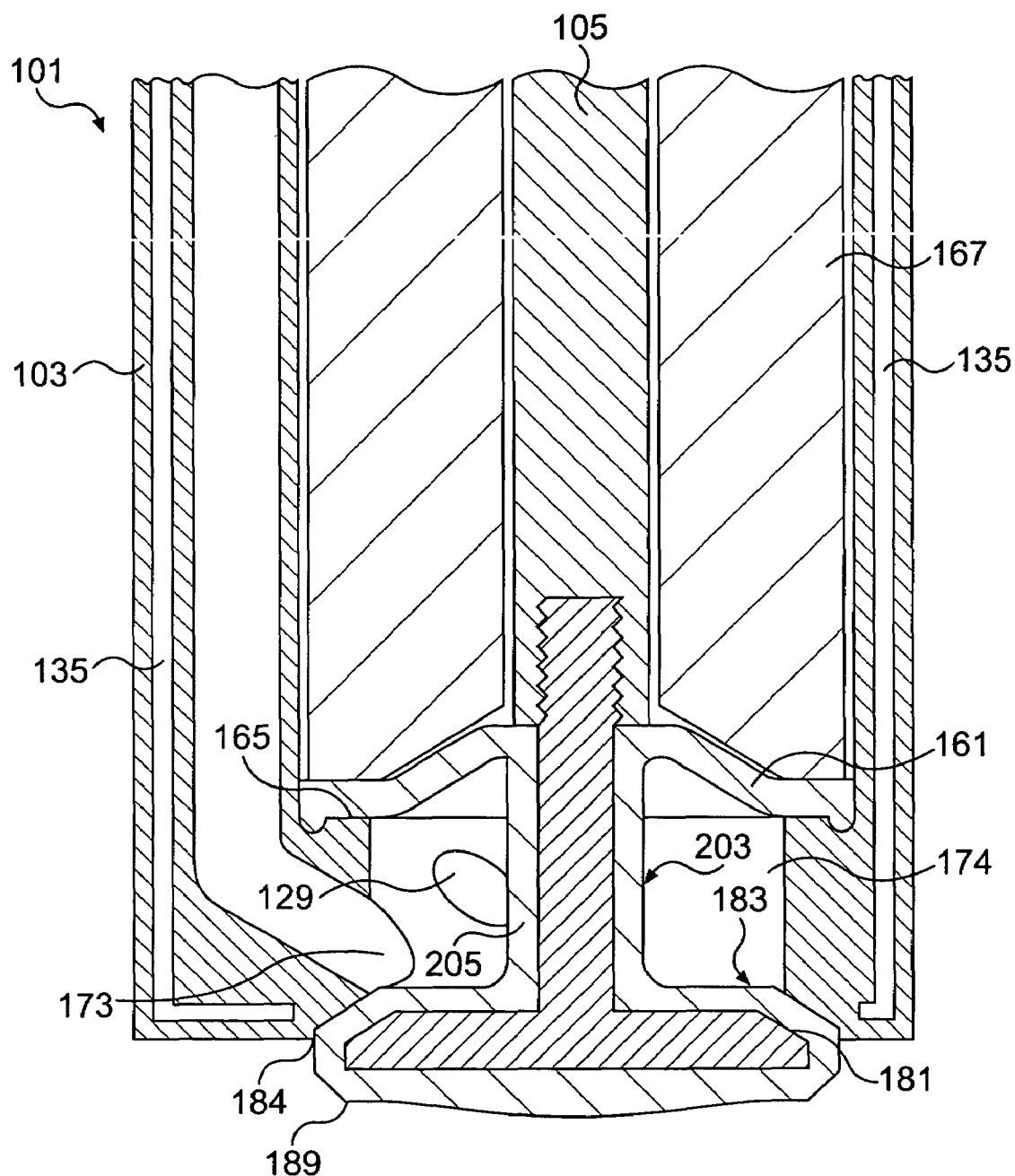
FIG. 10 is a cross-sectional view of a fifth embodiment of the present invention.

Referring to FIG. 10, a fifth embodiment of the present invention will be described. In FIG. 10, a one-piece member 203 is used in a similar manner to the embodiment of FIG. 3. The one-piece member includes a diaphram portion 161, a connecting portion 205 and a flexible outer covering 189. The one-piece member 203 has been used in place of the o-ring groove 122 and o-ring 124 of several of the previous embodiments. Of course, in FIG. 10 and the previous embodiments, the o-ring 124 could be included in addition to the one-piece member 203.

In FIG. 10, the valve actuating rod or shaft 105 is connected through a threaded connection to the sealing tip 181. The one-piece member 203 extends over the sealing tip 181 to seal between the external annular surface 184 of the body 103, which is adjacent to the orifice 183. The diaphram portion 161 of the one-piece member 203 is secured between an upwardly facing shoulder portion 165 of the body 103 and an inner cylinder or diaphram support member 167 to seal the moving components of the dip tube valve assembly 101 from the collection chamber 174 and the process within the vessel or conduit 102 (not shown in FIG. 10).

The above one-piece member 203 is similar to the embodiment of FIG. 3, except that both passages in FIG. 10 open into internal cavity 174 near orifice 183. Also, the distance between the seal with the external components and the collection chamber is much shorter. The cylindrical member 167 would be secured within the body 103 in the same manner as the embodiment of FIG. 3 with or without the cylindrical member 168 of FIG. 3. Also, cylindrical member 167 in FIG. 10 extends past flange 131, down to press against the outer radial portion of diaphragm portion 161. In addition, when assembling the valve components, it is preferred that the sealing tip 181 and one-piece member be installed from below the body 103, while the shaft 105 and the cylindrical member 167 be installed from above the body 103. The threaded tip, of the shaft 105 can easily be inserted into the mating threads of the sealing tip 181 to secure the assembly together.

Where insulation is desired, a space 135 can be provided within the wall of the body 103 to form an insulating jacket 133. The space 135 can be empty or an insulation material can be included therein, depending on the application, i.e., in situations where heat sensitive processes are within the vessel or conduit 102. As an alternative, the body 103 or other structural components of the dip tube valve assembly can be constructed of materials that inhibit heat transfer. In addition, where passive methods to curb heat transfer are not sufficient or desirable, active methods may also be used. Active methods include, but are not limited to, heating and cooling jackets and thermoelectric elements.

As can be clearly understood from FIG. 10, the inlet opening 129 and the drain opening 173 are located very close to the sealing tip 181. This enables the collection chamber 174 to be constructed much smaller than that shown in the first and second embodiments of the present invention. This smaller internal volume serves to conserve cleaning and sterilizing materials, reduces overall cleaning and sterilizing times and may serve to improve the overall cleaning, sterilizing, flushing and draining ability of the dip tube valve assembly 101.

As mentioned above, the seal at the orifice 183 has been described as being on the external annular surface 184 of the body 103, i.e., the process side of the orifice 183. However, it is also possible to form the seal on the non-process side of the orifice 183 by providing the sealing tip 181 within the internal cavity 174, which seals with an internal annular shoulder 219 of the body 103 (see FIG. 11A). In addition, if wiping or sliding seals can be tolerated for the dip tube valve assembly 101, then plunger, ball valve, butterfly and other sealing arrangements readily recognized to one having ordinary skill in the art are also within the scope of the present invention.

Figure 11A:
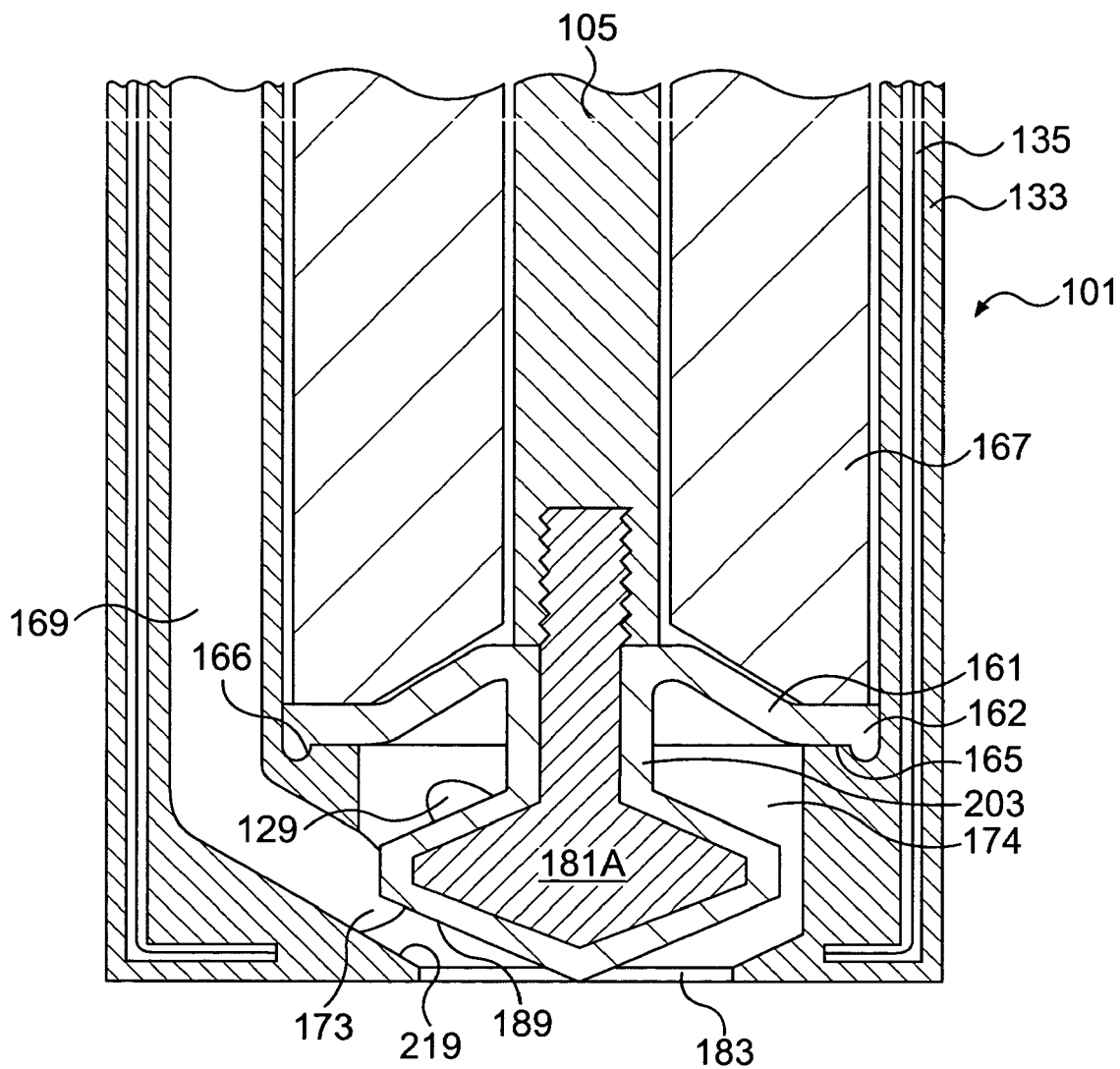
FIG. 11A is a cross-sectional view of a sixth embodiment of the present invention.

Referring to FIG. 11A, the sixth embodiment of the present invention is substantially the same as the fifth embodiment of the present invention, except that the sealing tip 181 seals about the orifice 183 with the inner annular shoulder 219 of the body 103. In this case, when assembling the dip tube valve assembly 101, the shaft 105, the cylindrical member 167, the one-piece member 203 and the sealing tip 181 are inserted from above the body 103.

Figure 11B:
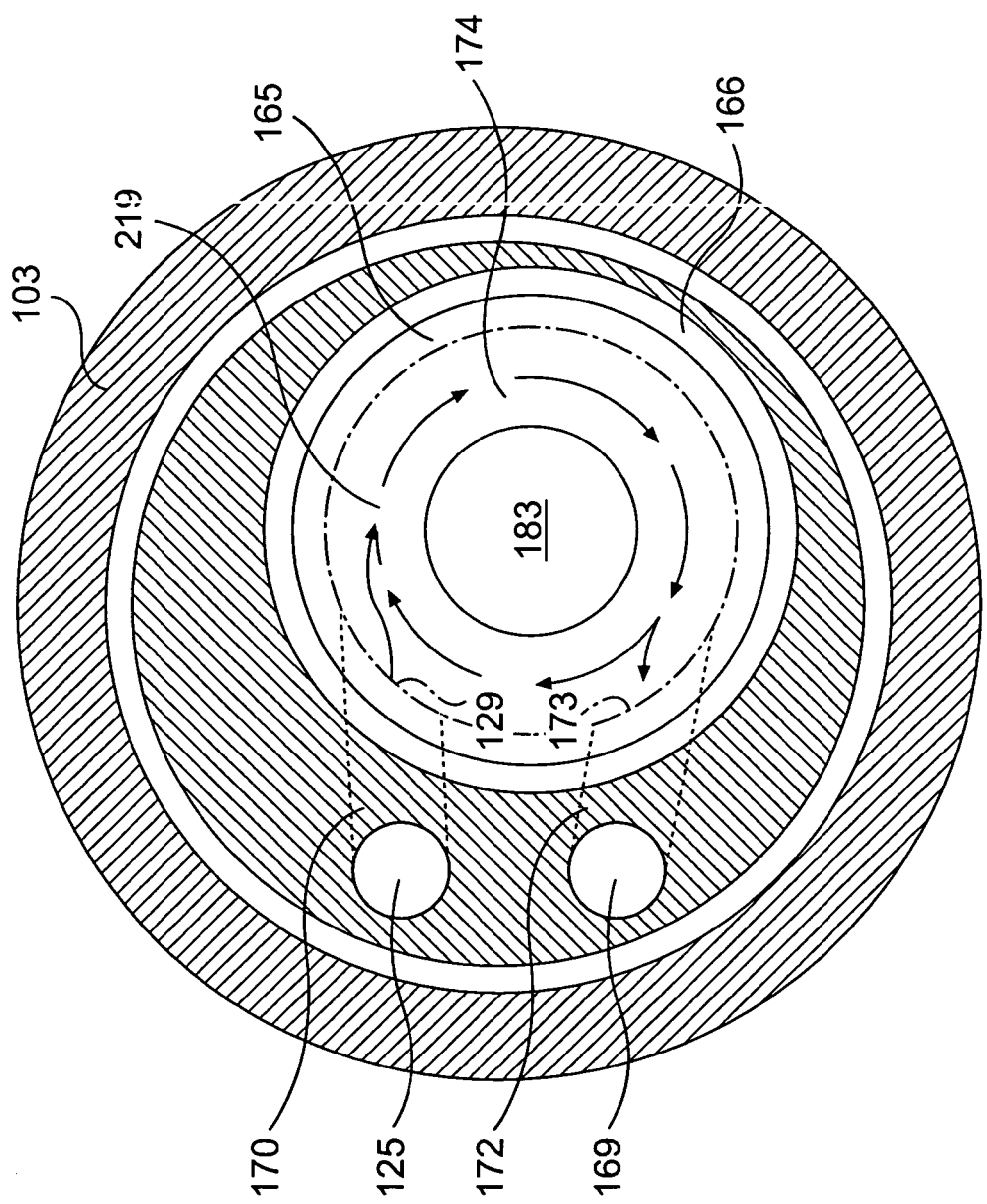
FIG. 11B is a cross-sectional view through a bottom of the sixth embodiment of FIG. 11A.

Referring to FIG. 11B, a cross-section through the collection chamber 174 of the embodiment of FIG. 11A is illustrated to show the orientation of the inlet passage 125 and the drain passage 169. The one-piece member 203, the shaft 105 and the cylindrical member 167 have been removed for clarity. The orifice 183, inner shoulder 219, upwardly facing shoulder portion 165 and a groove 166 for receiving an increased thickness portion 162 of the diaphragm portion 161 are illustrated. In addition, the vertical portion of the inlet passage 125 and the vertical portion of the drain passage 169 include a bent portion 170 and 172, respectively, which open into communication with the collection chamber 174 through inlet and outlet openings 129 and 173, respectively. In addition, FIG. 11B clearly shows how the positioning of the passages and other valve elements off center can allow the valve to be constructed in a compact manner.

As can be clearly understood from FIGS. 11A and 11B, when the sealing tip 181 is in the closed position (not illustrated in FIG. 11A), the flow proceeds through the inlet passage 125, the bent portion 170 and into the collection chamber 174 through the inlet opening 129 and scours the inside of the collection chamber 174. The flow then proceeds out of the drain opening 173, the bent portion 172 and up the drain passage 169.

With the above construction, the cleaning and flushing of the collection chamber 174 and other internal valve passages can be enhanced. It should also be noted that the inlet opening 129 and the drain opening 173 have been positioned to encourage vortex scouring through the collection chamber 174. In addition, the inlet opening 129 and the drain opening 173 have been located adjacent from each other, but pointing in opposite directions. This arrangement causes the drain passage to be open into the flow through the collection chamber 174, but only does so after the flow has traveled a maximum internal distance within the collection chamber 174. This increases the vortexing of the flow for scouring and flushing purposes, while minimizing the amount of short circuiting through the collection chamber 174 during maximum flow episodes.

Although the cross-section of FIG. 11B has been described as being through the bottom of the embodiment of FIG. 11A, it should be readily apparent to one having ordinary skill in the art that the same or similar orientation of the internal passages could also be applied to any of the previously or later described embodiments. Whether passages are located in the valve body walls or in the actuator shaft or a combination of both, passage openings may be oriented so as to create vortex flows as described above and to aid in the flushing of flows from the inlet, through the chamber or chambers (as will be discussed below) and out through the drain passage(s) or orifice(s).

Figure 12:
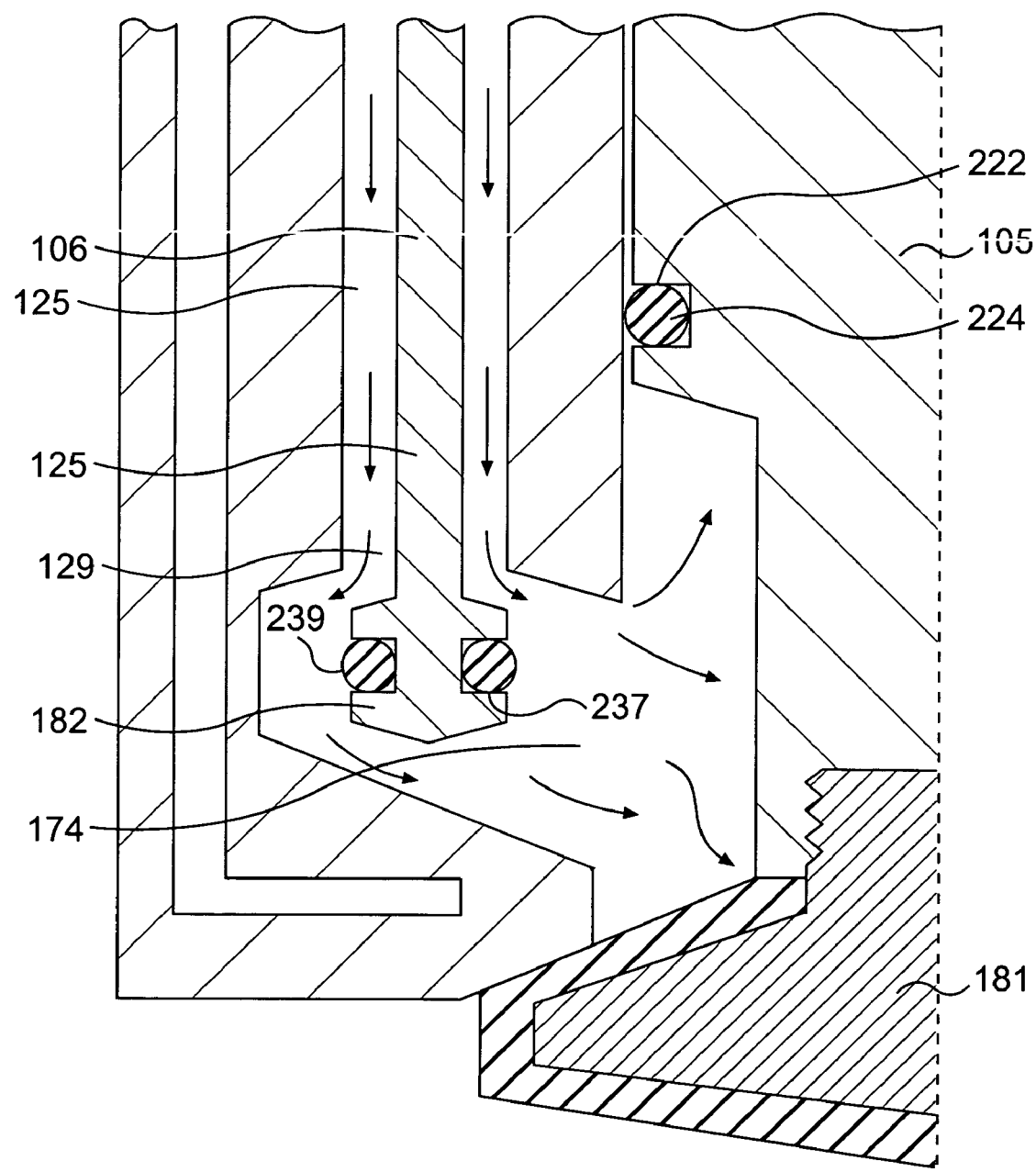
FIG. 12 is a partial, cross-sectional view of a seventh embodiment of the present invention.

Referring to FIG. 12, a seventh embodiment of the present invention will be described. In this embodiment, an additional shaft 106 is reciprocable within the inlet passage 125 to open and close the inlet opening 129. As an example of a means to seal, the shaft 106 includes an increased diameter sealing tip 182 which includes an o-ring groove 237 and o-ring 239, which seals the inlet opening 129. The sealing tip 182 provides the capability of closing the inlet passage 125 during removal of material from the process within the vessel or conduit 102 (not shown in FIG. 12) to prevent the material from backing up the inlet passage 125. Although the closing of a valve upstream from the inlet opening will form a vapor lock to prevent material from flowing up the inlet passage 125 to some extent, the use of the sealing tip 182 prevents any material from back flowing up the inlet passage 125 to thereby prevent any clogging of the inlet passage 125. The use of the sealing tip 182 is particularly useful in applications where the inlet passage 125 is used for the supply of air into the process, since the inlet passage 125 could be very narrow. However, the sealing tip 182 can be used in other inlet passages or outlet passages as well.

Figure 13:
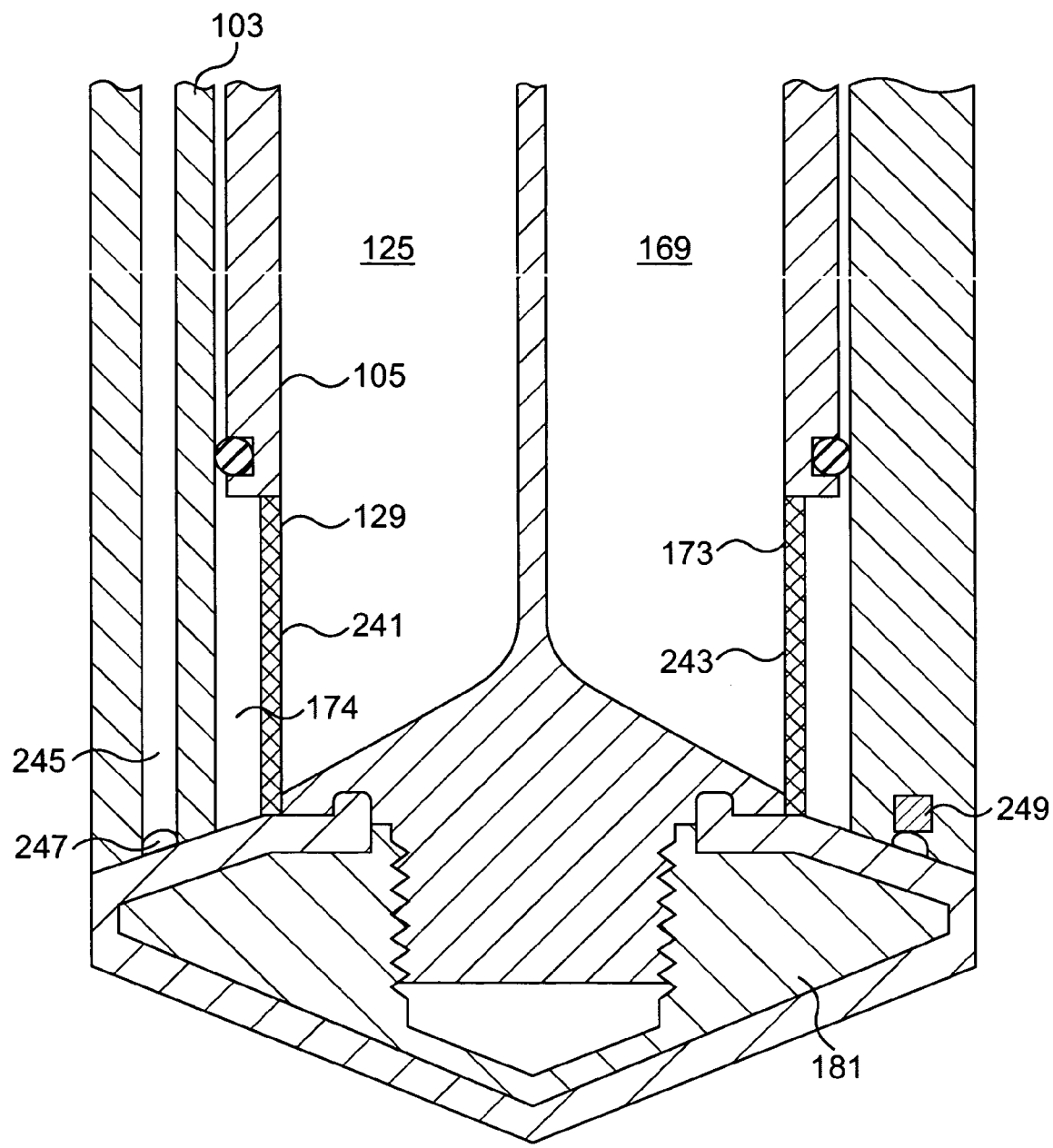
FIG. 13 is cross-sectional view of an eighth embodiment of the present invetion.

Referring to FIG. 13, an eighth embodiment of the present invention will be described. In this embodiment, the inlet passage 125 and the outlet passage 169 are formed within the shaft 105. The inlet opening 129 and the outlet opening 173 may, for example, be covered with porous membranes or disks 241 and 243, respectively. The porous disks 241 and 243 can be, for example, of sintered stainless steel material, airstone material, a perforated membrane, etc. to allow diffused air to be supplied into the process within the vessel or conduit 102 (not shown in FIG. 13). The use of porous disks to create fine streams of gas into a fluid process causes the creation of smaller bubbles than if the gas is supplied directly. Although forcing the gas through a porous structure results in reduced flow rates at a given supply pressure, the creation of the tiny bubbles, collectively, have a greater gas transfer surface area than do larger bubbles and so can result in greater gas transfer rates into solution. For many industrial processes, however, particularly those that are already highly mixed and where smaller bubbles are already being created by agitation or where the residence time of bubbles in the fluid column is large, creating small bubbles at gas supply openings may be of no benefit. In these cases, the porous boundaries would not be used and the gas would be supplied directly to the process.

For some applications where maximizing flow rates is of benefit such as is frequently the case in process aeration, flow may be increased by supplying flow through both outlet passages as well as through the inlet passages. In FIG. 13, for instance, inlet opening 129 and outlet opening 173 may both be moved into contact with the process so that gas can be supplied directly to the process through both openings. Later, when the valve needs to be recleaned, the valve tip may be retracted, resealing the valve, and the flow-through pattern (from inlet to chamber to outlet) cleaning can be re-established within the valve.

It should also be understood that it is possible to provide the porous membranes or disks in the passages of any of the embodiments of the present invention as well, depending on the application.

In addition, a passage 245 is formed in the body 103, which is in communication with an annular groove 247. As can be clearly understood, when the sealing tip 181 is in the closed position, a dual seal is formed with the body 103 on opposite sides of the annular groove 247. A sensor 249 can be included in communication with the annular groove 247 in order to provide an orifice seal leak prevention/detection. The sensor 249 can be, for example, a pH sensor, a pressure sensor, a temperature sensor, etc. to detect changes within the collection chamber 174 or the annular groove 249. The annular groove can be connected to a supply material at a higher pressure than the collection chamber to create an over pressure within the annular groove as a barrier to exchange between the process and the collection chamber 174.

As an alternative, an additional passage (not shown) could be formed in the body in communication with the annular groove 247, so that the passage 245 acts as an inlet passage and the additional passage acts as a drain passage. With this arrangement, a vacuum could be created downstream of the additional drain passage to capture leakage into the annular groove from the process within the vessel or conduit 102 or from the collection chamber 174. This will prevent the contamination of the process within the vessel or conduit 102. The addition of vacuum may also have the secondary effect of increasing seal integrity.

Figure 14:
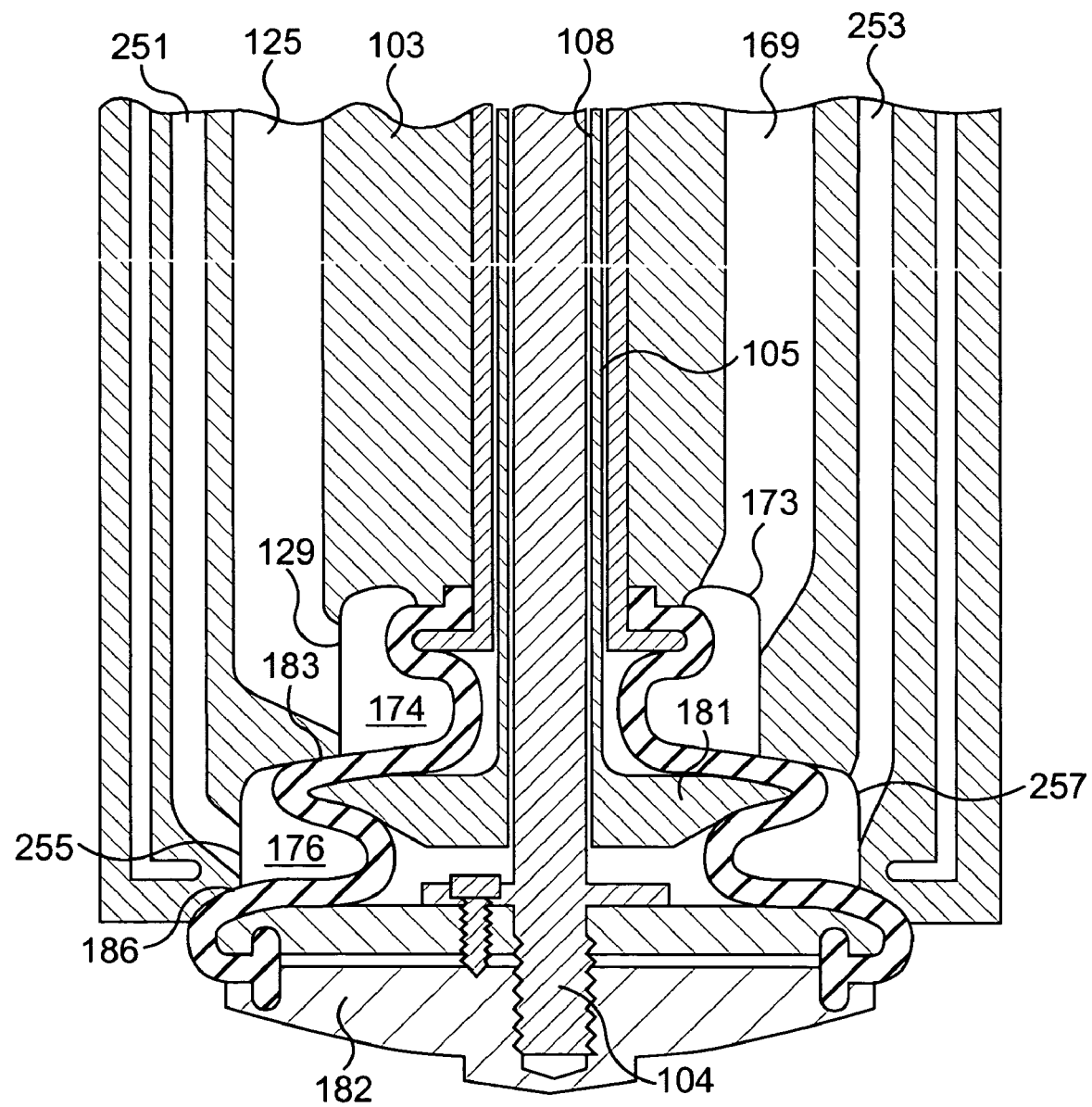
FIG. 14 is a cross-sectional view of a ninth embodiment of the present invention.
Figure 15:
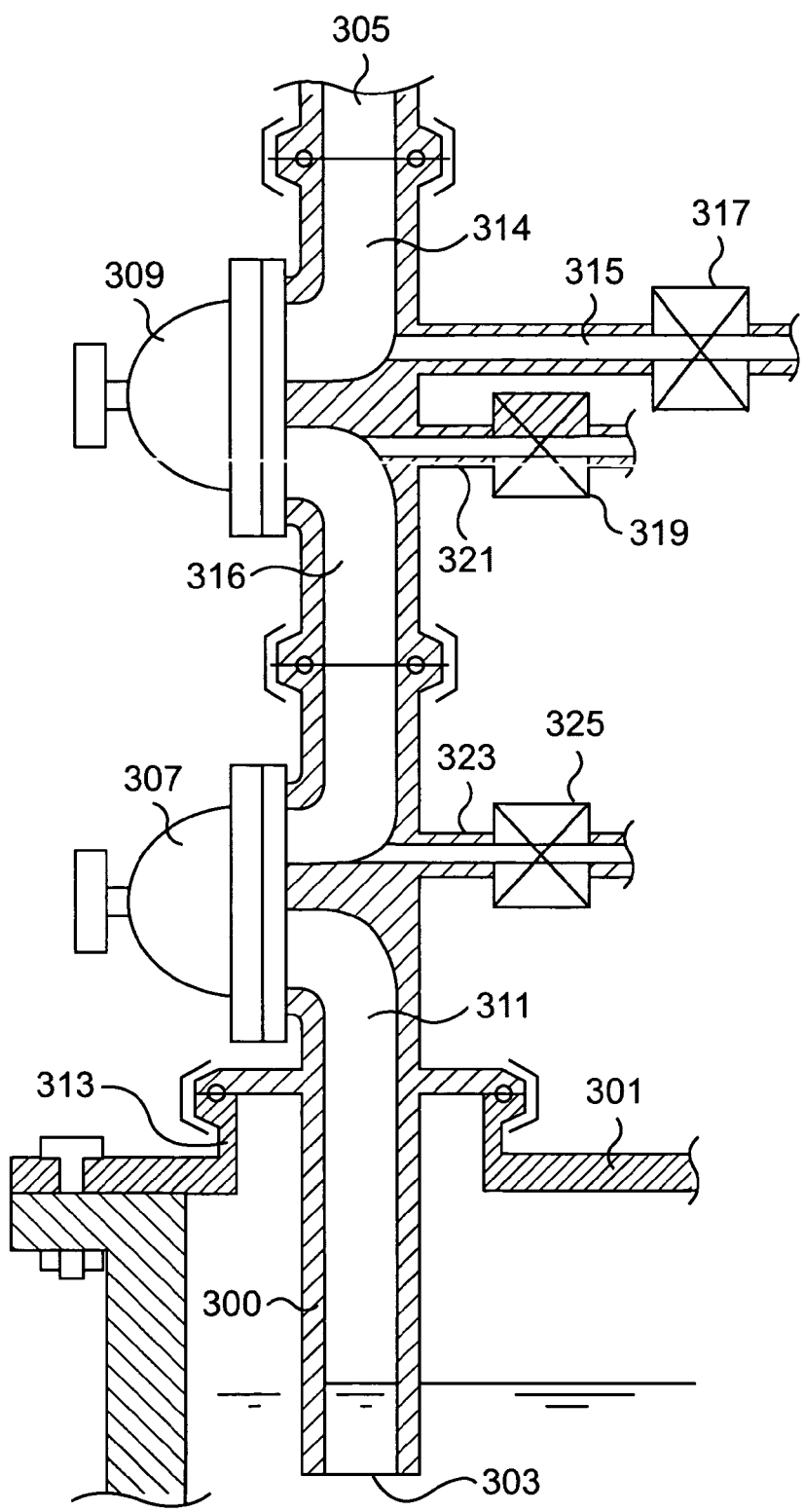
FIG. 15 is a cross-sectional view of a Background Art system.

Referring to FIG. 14, a ninth embodiment of the present invention will be described. In this embodiment, an upper collection chamber 174 and a lower collection chamber 176 are formed in the body 103. In addition, a primary inlet passage 125 and a primary drain passage 169 open into the upper collection chamber 174 through inlet openings 129 and 173, respectively. Furthermore, a secondary inlet passage 251 and a secondary drain passage 253 open into the lower collection chamber 176 through inlet and drain openings 255 and 257, respectively. As can be clearly understood, a primary shaft 105 includes a primary sealing tip 181 attached thereto for opening and closing the primary orifice 183, while a secondary shaft 104 includes a secondary sealing tip 182 attached thereto for opening and closing the secondary orifice 186.

It should be noted that the annular groove 247 in the embodiment of FIG. 13 is also considered to be a secondary collection chamber, but has been identified as a groove due to its small size. The important requirement to form primary and secondary collection chambers within the scope of the present invention is to have two chambers, which are separated from each other by an intermediate seal.

Referring again to FIG. 14, the primary shaft 105 includes an axial bore 108 therein, which receives the secondary shaft 104 for reciprocation. As can be clearly understood, a dual handwheel can be used to move the primary shaft 105 and the secondary shaft 104 independent of each other to selectively open and close the orifices 183 and 186, respectively. As an alternative, a pneumatic device could be used to operate the primary and secondary shafts 105 and 104. The operation of the primary and secondary shafts 105 and 104 would be well with the level of ordinary skill in the art and therefore will not be further described here.

As an alternative, both primary and secondary shafts may be formed as one shaft and the two sealing surfaces formed as sealing surfaces on one sealing tip, in this case, a stepped sealing tip. Such an arrangement would serve the purpose of simplifying the overall valve design while also providing seal redundancy. The spacing between sealing surfaces on the sealing tip or on the valve body may be adjusted so that one of the seals forms earlier and stronger than the other.

Where the process will allow, variations on the types of seals may also be used as mentioned earlier, and result in certain benefits such as less expensive variations on the principle designs presented here. For instance, in the case of an o-ring plunger design where the o-rings form seals along a uniform diameter cylindrical internal chamber wall, the internal chamber may be formed as a single cylindrical bore which, when the two o-rings seals are retracted, would form two chambers, one above the upper o-ring seal and one between the two o-ring seals. Many other variations on the general design concept will be apparent to anyone knowledgeable in the art.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for sampling or feeding a flowable material, comprising:
   a vessel or conduit having a wall;
   a body mounted to the wall of the vessel or conduit;
   a primary collection chamber formed in said body;
   a secondary collection chamber formed in said body;
   a primary drain passage, said primary drain passage having an opening operatively connected to said primary collection chamber;
   a secondary drain passage, said secondary drain passage having an opening operatively connected to said secondary collection chamber;
   a primary inlet passage for receiving flowable material therethrough, said primary inlet passage having an opening in communication with said primary collection chamber;
   a secondary inlet passage for receiving flowable material therethrough, said secondary inlet passage having an opening in communication with said secondary collection chamber;
   an orifice formed in said body and in communication with said primary collection chamber, said orifice being located generally adjacent said opening of said primary drain passage; and
   a sealing device, said sealing device being mounted to said body to seal and unseal said orifice,
   wherein at least a portion of said opening of said primary drain passage is located flush with or inside of the vessel or conduit.

2. The apparatus for sampling or feeding a flowable material according to claim 1, wherein said primary collection chamber and said secondary collection chamber are located adjacent to each other, said primary orifice is a primary orifice and is located between said primary collection chamber and said secondary collection chamber, and said sealing device is a primary sealing device, said apparatus further comprising:

a secondary orifice, said secondary orifice being formed in said body and in communication with said secondary collection chamber, said secondary orifice being located generally adjacent the opening of said secondary inlet and outlet passages; and a secondary sealing device, said secondary sealing device being mounted to said body to seal and unseal said secondary orifice.

3. The apparatus for sampling or feeding a flowable material according to claim 1, further comprising a sensor, said sensor being operatively connected to at least one of said primary and secondary collection chambers for sensing conditions within said at least one of said primary and secondary collection chambers or conditions of said sealing device.

4. An apparatus for sampling or feeding a flowable material through a wall of a vessel or conduit comprising:

a body;

a primary collection chamber formed in said body;

a primary passage, said primary passage having an opening operatively connected to said primary collection chamber;

a secondary collection chamber formed in said body; and a secondary passage, said secondary passage having an opening operatively connected to said secondary collection chamber;

an orifice formed in said body and in communication with said primary collection chamber, said orifice being located generally adjacent said opening of said primary passage; and a sealing device, said sealing device being mounted to said body to seal and unseal said orifice, wherein said primary passage is a primary drain passage and said secondary passage is a secondary drain passage, said apparatus further comprising:

a primary inlet passage for receiving flowable material therethrough, said primary inlet passage having an opening in communication with said primary collection chamber; and a secondary inlet passage for receiving flowable material therethrough, said secondary inlet passage having an opening in communication with said secondary collection chamber.

5. The apparatus for sampling or feeding a flowable material through a wall of a vessel or conduit according to claim 4, wherein said primary collection chamber and said secondary collection chamber are located adjacent to each, said orifice is a primary orifice and is located between said primary collection chamber and said secondary collection chamber, and said sealing device is a primary sealing device, said apparatus further comprising:

a secondary orifice, said secondary orifice being formed in said body and in communication with said secondary collection chamber, said secondary orifice being located generally adjacent said opening of said secondary inlet and outlet passages; and a secondary sealing device, said secondary sealing device being mounted to said body to seal and unseal said secondary orifice.

6. The apparatus for sampling or feeding a flowable material through a wall of a vessel or conduit according to claim 4, further comprising a sensor, said sensor being operatively connected to at least one of said primary and secondary collection chambers for sensing conditions within said at least one of said primary and secondary collection chambers or conditions of said sealing device.

7. An apparatus for sampling or feeding a flowable material through a wall of a vessel or conduit comprising:

a body;

a primary collection chamber formed in said body;

a primary passage, said primary passage having an opening operatively connected to said primary collection chamber;

a secondary collection chamber formed in said body; and a secondary passage, said secondary passage having an opening operatively connected to said secondary collection chamber;

an orifice formed in said body and in communication with said primary collection chamber, said orifice being located generally adjacent said opening of said primary passage;

a sealing device, said sealing device being mounted to said body to seal and unseal said orifice; and a sensor, said sensor being operatively connected to at least one of said primary and secondary collection chambers for sensing conditions within said at least one of said primary and secondary collection chambers or conditions of said sealing device.

8. The apparatus for sampling or feeding a flowable material through a wall of a vessel or conduit according to claim 7, wherein said primary collection chamber and said secondary collection chamber are located adjacent to each other, said orifice is a primary orifice and is located between said primary collection chamber and said secondary collection chamber, and said sealing device is a primary sealing device, said apparatus further comprising:

a secondary orifice, said secondary orifice being formed in said body and in communication with said secondary collection chamber, said secondary orifice being located generally adjacent the opening of said secondary passage; and a secondary sealing device, said secondary sealing device being mounted to said body to seal and unseal said secondary orifice.

* * * * *